US005474574A

United States Patent [19]
Payne et al.

[11] Patent Number: 5,474,574
[45] Date of Patent: Dec. 12, 1995

[54] AUTOMATIC EXTERNAL CARDIOVERTER/DEFIBRILLATOR

[75] Inventors: Errol G. Payne, Newport Beach; Howard K. Cooper, Woodland Hills; Prabodh Mathur, El Toro; Joseph P. Seemann, Mission Viejo; Vahid Saadatmanesh, Tustin; Michael A. Brodsky, Long Beach; Glenn D. Yeik, Escondido, all of Calif.

[73] Assignee: Cardiac Science, Inc., Irvine, Calif.

[21] Appl. No.: 903,671

[22] Filed: Jun. 24, 1992

[51] Int. Cl.$^6$ ........................................ A61N 1/39
[52] U.S. Cl. ........................................ 607/7
[58] Field of Search ............... 607/4, 5, 6, 7, 607/8

[56] References Cited

U.S. PATENT DOCUMENTS

| | | | |
|---|---|---|---|
| Re. 27,757 | 9/1973 | Mirowski | 607/5 |
| 2,943,628 | 7/1960 | Howell | 607/5 |
| 3,093,136 | 6/1963 | Lohr | 607/5 |
| 3,138,151 | 6/1964 | Chapman et al. | 607/5 |
| 3,241,556 | 3/1966 | Zacouto | 607/5 |
| 3,426,746 | 2/1969 | Seamans, Jr. | 607/5 |
| 3,460,542 | 8/1969 | Gemmer | 607/5 |
| 3,464,404 | 9/1969 | Mason | 607/5 |
| 3,702,613 | 11/1972 | Panico et al. | 607/5 |
| 3,805,795 | 4/1974 | Denniston et al. | 607/5 |
| 3,826,245 | 7/1974 | Funfstuck | 607/5 |
| 3,857,398 | 12/1974 | Rubin | 607/5 |
| 3,942,533 | 3/1976 | Cannon, III | 607/5 |
| 3,942,536 | 3/1976 | Mirowski et al. | 607/5 |
| 3,961,623 | 6/1976 | Milani et al. | 607/5 |
| 4,002,239 | 1/1977 | Buchalter | 607/5 |
| 4,023,573 | 5/1977 | Pantridge et al. | 607/5 |
| 4,058,127 | 11/1977 | Buchalter | 607/5 |
| 4,088,138 | 5/1978 | Diack et al. | 607/5 |
| 4,096,856 | 6/1978 | Smith et al. | 607/5 |
| 4,129,125 | 12/1978 | Lester et al. | 607/5 |
| 4,243,051 | 1/1981 | Wittemann | 607/5 |
| 4,369,284 | 1/1983 | Chen | 607/5 |
| 4,576,170 | 3/1986 | Bradley et al. | 607/5 |

(List continued on next page.)

OTHER PUBLICATIONS

RJP Associates brochure.
"First Responders Can Make A Critical Difference!" CRC product brochure, Sep. 1987.
"In Your Hands This Can Save A Life", CRC product brochure, Apr. 1982.
"First In Instant Pacing!", CRC product brochure, 1982.
"Heart Aid", CRC product brochure.
"Lifesaving Device to Jump–Start Failing Hearts Proves Successful", newspaper article.
"If Stricken by a Heart Attack, Best Place to Be Is in Seattle", *Wall Street Journal*.
CRC newsletter, *the Heart Beat*, vol. 1, No. 1, Feb. 1983.

*Primary Examiner*—William E. Kamm
*Attorney, Agent, or Firm*—Knobber, Martens Olson & Bear

[57] ABSTRACT

A cardiac monitoring and defibrillation system is provided which may be embodied as a bedside unit or as an ambulatory unit. The system includes amplification and processing circuitry which receives and conditions inputs from a variety of sensing means such as an electrocardiogram, a blood oxygenation sensor, a blood pressure monitor, and a cardiac acoustical transducer. A noise and artifact discrimination procedure is employed to prevent erroneous detection of the onset of cardiac arrhythmias. In response to the conditioned inputs from the monitoring means, the microprocessor controls therapeutic electrical stimulus which may be delivered to a patient in accordance with a cardioverter/defibrillator step therapy method. The microprocessor may be operated or programmed by means of a control panel or an external programming and monitoring unit. In one embodiment, the system includes a bidirectional communication link which allows the microprocessor to be monitored and programmed by a physician at a remote location. Furthermore, the system provides a method for detecting cardiac arrhythmias and distinguishing between the different types of arrhythmias which may be detected.

14 Claims, 10 Drawing Sheets

U.S. PATENT DOCUMENTS

| | | | |
|---|---|---|---|
| 4,618,213 | 10/1986 | Chen | 607/5 |
| 4,729,377 | 3/1988 | Granek et al. | 607/5 |
| 4,928,690 | 5/1990 | Heilman et al. | 607/5 |
| 5,014,697 | 5/1991 | Pless et al. | 607/5 |
| 5,014,698 | 5/1991 | Cohen . | |
| 5,111,813 | 5/1992 | Charbonnier et al. | 607/5 |
| 5,156,148 | 10/1992 | Cohen | 607/5 |

AUTOMATIC EXTERNAL CARDIOVERTER/DEFIBRILLATOR

BACKGROUND OF THE INVENTION

1. Field of the Invention

The present invention relates to heart monitoring and non-surgical, automatic cardioverter/defibrillator devices.

2. Description of the Related Art

Sudden Cardiac Death (SCD) is the leading single cause of death in the United States today. SCD frequently results from the precipitous onset of electrical instability in the auto-nervous system which regulates the beating of the heart. This electrical instability may result in the development of catastrophic cardiac ventricular arrhythmia, which in most cases, if therapeutic or resuscitative measures are not taken immediately, can lead to serious injury or death.

Studies have shown that the most frequent arrhythmias recorded by emergency medical response teams are ventricular fibrillation (quivering of the heart) and ventricular tachycardia (dangerously fast heart rate). The conditions which indicate the onset of ventricular fibrillation and ventricular tachycardia include irregular and/or dangerously fast electrical impulses transmitted to the heart, and a lowering of the blood oxygenation level and blood pressure. Thus, it is possible to monitor these conditions in order to detect the onset of either ventricular fibrillation or ventricular tachycardia.

In addition to anti-arrhythmic drugs, therapeutic electrical devices are available for the management of such abnormal heart rhythms. For instance, implantable cardioverter/defibrillators (ICDs) are available to control ventricular tachyarrhythmias and fibrillation. These devices are implanted in a patient with electrodes attached directly to the heart. ICDs automatically sense the onset of life threatening arrhythmias and apply electrical energy pulses, which are synchronized with a detected heart beat during cardioversion to stabilize cardiac impulses produced by the auto-nervous system. This procedure for restoring normal heart functions is commonly known as cardioversion or defibrillation. Implantable pacemakers are also available, typically to provide bradycardia pacing of the heart when the heart rate is too slow.

ICDs are often implanted in persons who are known to suffer from recurring ventricular tachycardia and/or ventricular fibrillation, particularly when drug therapy is ineffective. Because ICDs are automatic and implanted in the patient, they allow a patient to remain ambulatory even when the patient may be at risk of ventricular tachycardia or ventricular fibrillation. Thus, ICD patients are often able to carry on a somewhat normal lifestyle. Otherwise, these patients are often confined by constant medical care requirements or they risk SCD. However, ICDs require surgery with many accompanying risks.

External, yet portable automatic defibrillator devices have also been proposed. For instance, U.S. Pat. No. 4,576,170 proposes a portable automatic defibrillator. However, a number of serious limitations have hampered the development of such devices, particularly ambulatory devices. For instance, a significant amount of signal noise and artifact are associated with externally monitoring the condition of a patient's heart beat. Thus, accurate analysis of the signals is difficult. This is often due to the movement and activity of the person wearing the device.

Because of the noise and artifacts present in external monitors, the state-of-the art heart monitoring devices may fail to accurately detect an abnormal or unsatisfactory cardiac rhythm. In addition, these monitoring devices could misinterpret the signal variations caused by noise and artifact as the onset of an abnormal condition, causing the defibrillator system to initiate unnecessary corrective therapy. The unnecessary initiation of therapy can create a state of electrical instability which may cause the onset of ventricular fibrillation, thereby placing the patient's life at risk.

A further limitation of existing and proposed devices is that they are limited in their adaptability from patient to patient. The devices have parameters predefined which generalize the detection of arrhythmias and the therapy administered

SUMMARY OF THE INVENTION

The present invention is an external cardiac monitor and cardioverter/defibrillator system which provides a significant advance in the field with a device which effectively discriminates between signals that represent the actual condition of a patient's heart, and signal noise or artifact. Based on these signals, the system automatically delivers or withholds therapy according to parameters preferably selected through programming by the physician.

The system comprises a cardiac monitor system in conjunction with electronic cardioverter/defibrillator circuitry which are controllable by a microprocessor. The microprocessor obtains data from signals provided by one or more ECG sensors, and a plurality of optional secondary sensors. The operation of the microprocessor is responsive to programmable variables which may be input into the system by means of a control panel, or by means of a bidirectional communications link. A significant feature of the present invention is that it is highly programmable and adaptable to each patient's individual cardiac conditions. This programming capability provided by the present invention increases the system's capacity to be adapted to a particular patient's needs. For instance, the physician may desire to alter the parameters affecting the determination of ventricular tachycardia and ventricular fibrillation and/or alter the programmed therapy.

The system of the present invention also has the advantage that it may be implemented either as a battery operated ambulatory system or as a compact bedside device.

The method of the present invention involves properly analyzing cardiac signals in the presence of noise and artifact signals. In one embodiment, the unit utilizes primary sensors and also utilizes secondary sensors to verify the information received by the primary sensors.

A further advantage of the system of the present invention is that it detects and discriminates between different types of cardiac arrhythmias. The detection of the different types of arrhythmias is based upon such criteria as morphology, heart rate, and irregularity of the heart rate over different time intervals.

Once the abnormality is detected and classified, the invention provides a method for effectively treating the abnormal rhythm by means of a series of therapeutic electrical energy pulses which are delivered at selected time intervals and at selected energy levels and/or by means of delivery of therapeutic drugs as determined by the patient's physician in programming the system's parameters.

One aspect of the present invention involves a programmable external cardioverter/defibrillator device for automatically detecting cardiac arrhythmias and administering therapy. The device effectively discriminates between signals received from a patient that represent the actual condition of a patient's heart and signal noise or artifact. The system is further adaptable in detection and therapy from patient to patient. The system has at least one sensor adapted for external application to a patient. The sensor detects cardiac signals from the patient and produces a detection signal representing the cardiac signals. A signal noise and artifact discrimination controller filters noise and artifact from the detection signal so that the system can accurately detect the actual condition of the patient's heart. Programmable control circuitry has a parameter memory adapted to receive and store vital parameters which are changeable by an operator. The control circuitry also has processing logic coupled to the parameter memory, and the processing logic responds to the detection signal and the parameters in the parameter memory to automatically detect and identify cardiac arrhythmias and to automatically produce control signals. The processing logic further selects a first predetermined energy based on the stored parameters to be delivered for electrical therapy when an arrhythmia is detected. The first predetermined energy is based upon the arrhythmia identification. In one embodiment, to deliver the first predetermined energy, the processing logic further determines the impedance between at least two energy delivery electrodes and, in response to the impedance and predetermined energy level, adjusts a voltage to be applied across the energy delivery electrodes so that the energy delivery electrodes deliver the first predetermined energy. After electrical therapy delivery, the processing logic further monitors the detection signal for a time interval sufficient to determine if cardioversion or defibrillation has occurred, and automatically selects and delivers a second predetermined energy based on the stored parameters if cardioversion or defibrillation has not occurred. The control signals indicate the energy level and the appropriate voltage when an arrhythmia has been detected. Cardioverter/defibrillator circuitry coupled to at least two energy delivery electrodes responds to the control signals to automatically deliver therapeutic electrical stimuli via the energy delivery electrodes at varying levels of intensity (multiple predetermined energies) when an arrhythmia has been detected.

DETAILED DESCRIPTION OF THE INVENTION

Figure 1:
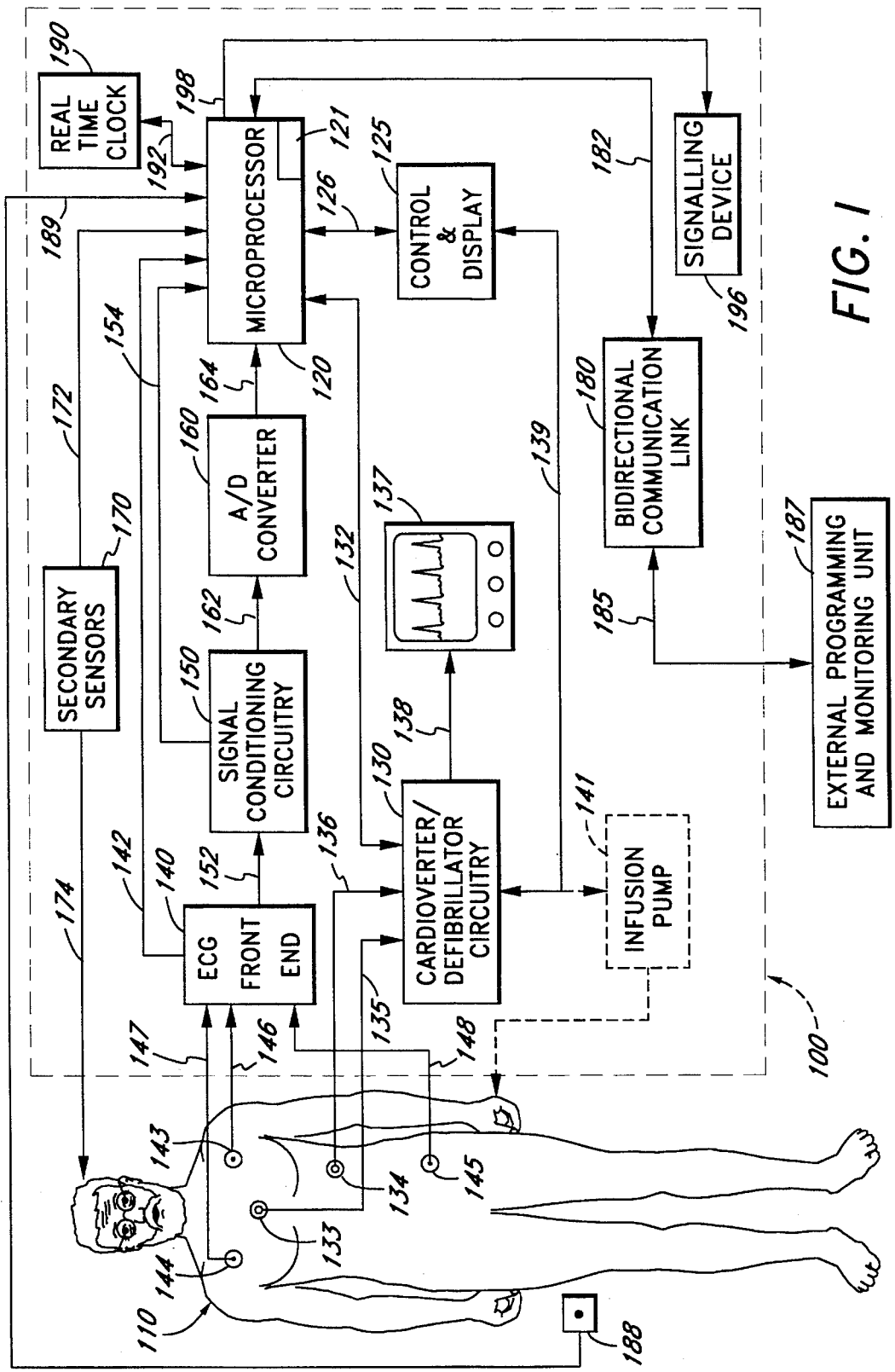
FIG. 1 is a simplified block diagram of the major functional elements of the heart monitor and cardioverter/defibrillator device.

FIG. 1 is a simplified block diagram of a heart monitor and cardioverter/defibrillator system 100 constructed in accordance with the present invention. The system 100 is an external cardiac monitor and cardioverter/defibrillator which is depicted connected to a patient 110. Through sensors, the system 100 monitors the signals from the patient's heart and automatically detects abnormal heart rhythms. If an abnormal heart rhythm is detected, the system 100 further classifies the abnormality and determines if electrical (and/or drug therapy in one embodiment) is warranted. If therapy is necessary, the system 100 automatically delivers electrical and/or drug therapy in order to return the patient's heart to a normal cardiac rhythm. The system 100 as described may be implemented as an ambulatory or portable monitor and cardioverter/defibrillator device, or as a convenient and compact bedside monitor and cardioverter/defibrillator system. In addition, in one embodiment, the system 100 may also provide pacing capabilities for maintaining normal heart rhythms in persons having abnormally slow heart rates. The system is programmable in order to adapt the automatic detection and therapy administration for the particular patient. Moreover, the system accurately discriminates between the signals which represent the condition of the patients heart and the noise and artifact which are often present because the sensors connect externally to the patient.

The system 100 is connected to a patient 110 so that the system 100 monitors the electrical impulses which indicate the beating of the patient's heart, as well as other critical factors which may be used to determine the cardiac condition of the patient 110. The system 100 has a microprocessor based system 120, which may, for example include a 68HC11 microprocessor available from Motorola. The microprocessor based system 120, is hereinafter referred to as the microprocessor 120, although it should be understood that the microprocessor 120 includes memory and conventional interface and peripheral circuitry which allow the microprocessor 120 to communicate with the other components of the system 100. Particularly, the microprocessor 120 of the present invention has a parameter memory 121 which stores programmable parameters as explained further herein. Desirably, the parameter memory 121 may comprise a non-volatile random access memory so that the memory maintains the information even in a power loss to the system 100. The microprocessor 120 is connected to control and display circuitry 125 via control lines 126.

Figure 2:
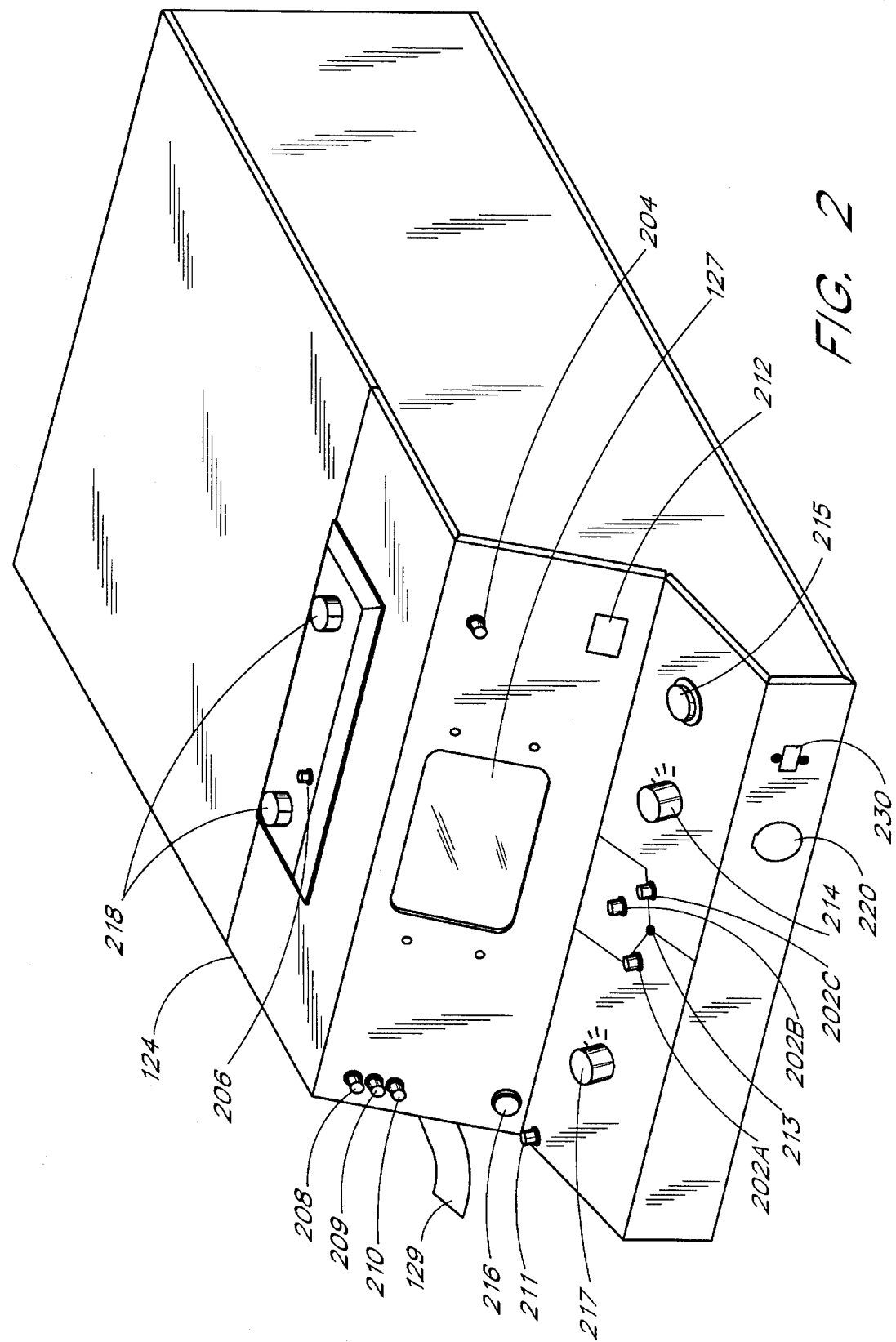
FIG. 2 is a perspective view of one possible control and display panel used in accordance with the present invention.

A perspective view of one embodiment of a control and display panel 124 is shown in FIG. 2. In one implementation, the control and display panel 124 may include an electroluminescent display 127, sold by Sharp, Inc. and a conventional strip chart recorder 129. The panel 124 includes various indicators which may be used to display the status of selected critical parameters which relate to the cardiac status of the patient 110. For example, in the embodiment shown, the control and display panel 124 has mode indicators 202A, 202B, 202C, a heart beat indicator 204, a ready to discharge indicator 206, an ECG leads off indicator 208, a defibrillator leads off indicator 209, a low battery indicator 210, and a reset required indicator 211. In another embodiment, the device may also include heart rhythm indicators (e.g., non-shockable rhythm, ventricular tachycardia, ventricular fibrillation, and unrecognized rhythm indicators). The panel 124 also includes a plurality of controls, which may comprise dials, switches, buttons or other input devices which may be manually adjusted by the user. The controls may be used to set specified system parameters, to control selected functions of the system 100, and to input data relating to the patient's condition. In the embodiment depicted in FIG. 2, the control and display panel 124 has a power control 212, a mode control 213, an energy select control 214, a charge control 215, a strip chart control 216, a ventricular tachycardia (VT) rate cutoff control 217, and discharge controls 218. The control and display panel 124 may also include connection terminals (not shown) for connecting to an external display, as well as to other components of the system 100. Further, the panel 124 has connection terminals 220 for ECG sensing electrodes and connection terminals 230 for energy delivery electrodes 133, 134 (FIG. 1).

The microprocessor 120 connects to cardioverter/defibrillator circuitry 130 (FIG. 1) via a conventional bidirectional bus 132 or with other conventional control lines. The cardioverter/defibrillator circuitry 130 may include conventional circuitry such as a capacitor for storing energy, and charge and discharge circuitry (not shown). The cardioverter/defibrillator 130 is connected to electrical therapy delivery electrodes 133, 134 via lines 135, 136. The delivery electrodes 133, 134 are preferably fastened to the torso of the patient 110 so that therapeutic electrical pulses may be administered to the patient 110 by means of the electrodes 133, 134. The electrodes 133, 134 may be connected on the surface of the skin, subcutaneously, or submuscularly depending upon the needs of the patient 110. They may also be applied to the torso by an operator holding standard defibrillator paddles.

The cardioverter/defibrillator circuitry 130 may be connected to an optional display 137 via lines 138 via a terminal (not shown) on the panel 124. Control and display circuitry 125 is connected to the cardioverter/defibrillator circuitry 130 via lines 139. In one embodiment, the control and display circuitry 125 may connect to a drug administering infusion pump 141 which is configured to administer drugs intervenously to the patient 110 via a catheter 143 or the like. The microprocessor 120 is further connected to an electrocardiograph (ECG) front end 140. The ECG front end 140 is connected to the patient 110 via sensing electrodes 143, 144 and 145 on the torso of the patient 110. The electrodes 143–145 are electrically connected to the ECG front end 140 via lines 146–148 (via the connection 220 on the control and display panel 124). The ECG front end 140 is further connected to signal conditioning circuitry 150 via signal lines 152. Advantageously, the signal conditioning circuitry 150 includes a variable gain amplifier which automatically adjusts the amplification of the ECG signal to compensate for changes in the amplitude of the detected ECG signal. The signal conditioning circuitry 150 is connected to the microprocessor 120 via signal lines 154. The signal conditioning circuitry 150 is also connected to an analog-to-digital converter 160 via signal lines 162. The analog-to-digital converter 160 is connected to the microprocessor 120 via signal lines 164.

In the embodiment shown, the microprocessor 120 is also connected to secondary sensors 170 via signal lines 172. The secondary sensors 170 may include, for instance, a photo-optical blood oxygenation sensor, an acoustical transducer such as a cardiac microphone, a pressure measurement system to measure the systolic and diastolic blood pressure, or other sensing devices which may be used to monitor the cardiac condition of the patient 110. The secondary sensors 170 may be attached to appropriate areas on the patient 110 via lines 174.

The microprocessor 120 is further connected to a bidirectional communication link 180 via signal lines 182. The communication link may comprise, for example, a two-way radio transmitter/receiver, a telephone modem, or any other bidirectional communication means which are appropriate to transmit information relating to the cardiac status of the patient 110. The bidirectional communication link 180 is adapted to connect to a system external programming and monitoring unit 187 via signal lines 185.

In one embodiment, the microprocessor 120 is connected to a user inhibit button 188 via signal lines 189. The user inhibit button 188 may be depressed by the patient 110 in order to inhibit the administration of defibrillation or cardioversion therapy if the patient 110 feels that impending therapy is not necessary. The microprocessor 120 may also be connected to a real-time clock 190 via a bidirectional bus 192. The clock 190 allows the system 100 to maintain a real-time account of the cardiac status of the patient 110 so that significant events may be labeled with the time and date at which they occurred for future analysis. In one embodiment, the microprocessor 120 could be connected to a signalling device 196 via signal lines 198 so that user discernable signals may be transmitted to the user of the system 100. The signals could be audible tones, vibrations or other signals discernable by the wearer and/or attendant, and the signalling device 196 would be a device to provide the desired signal.

In addition to those components described above, one embodiment of the system 100 may also include optional data acquisition and storage components for continuous storage of ECG data which is acquired, stored, and displayed before, during, and following any episode or multi-episodes requiring electric pulse therapy. Furthermore, components for storing other data associated with an event such as, but not limited to the date and time of an event, the amount of energy delivered, and the response of the patient 110 to the delivered energy. In one embodiment, these components may be a disk storage and retrieval system connected directly to the microprocessor 120 or may be connected by means of additional interface circuitry such as a disk operating system (DOS) controller.

As explained above, the system may be implemented as a bedside unit or as an ambulatory unit. The bedside embodiments of the system 100 may be powered through a standard power outlet and have an AC/DC power supply (not shown) which steps down and converts the voltage to that necessary to operate the computer and other circuitry in the system. However, one embodiment of the system may also be adapted to utilize a rechargeable battery power system similar to those used for portable and notebook computers (not shown). The battery could power the system in case of a power outage or allow the system to be used as an ambulatory unit. Preferably, in an embodiment configured as an ambulatory unit, the system 100 would not include the external display 137, the internal display 127 incorporated with the unit, the strip chart recorder 129, the AC/DC power supply and the DOS controller. Eliminating these elements would eliminate weight, as well as power consumption items, thereby prolonging the battery life.

Figure 7:
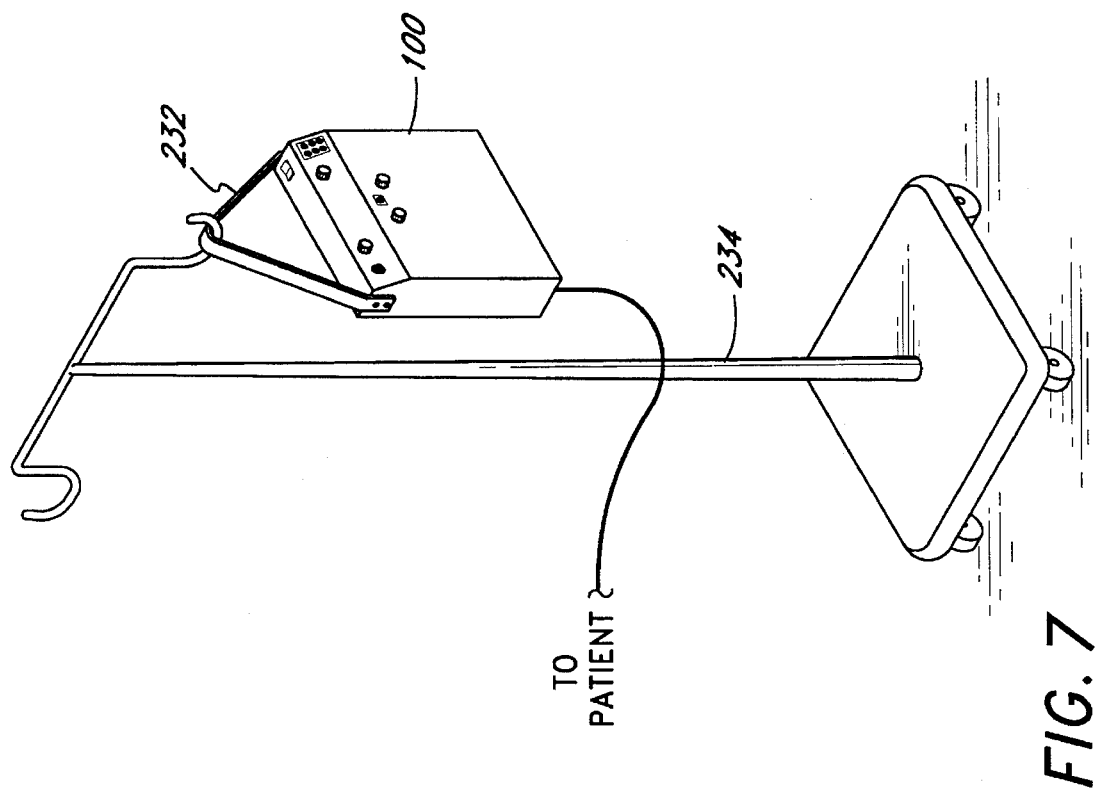
FIG. 7 is a diagram illustrating a possible ambulatory embodiment according to the present invention.

FIG. 7 illustrates a possible ambulatory embodiment, particularly useful at a medical care facility. The ambulatory embodiment of FIG. 7 has a carrying strap 232 which would allow the system 100 to be hung on a conventional IV pole 234 with wheels. This would allow a patient to walk around a hospital while remaining connected to the system 100.

Figure 8:
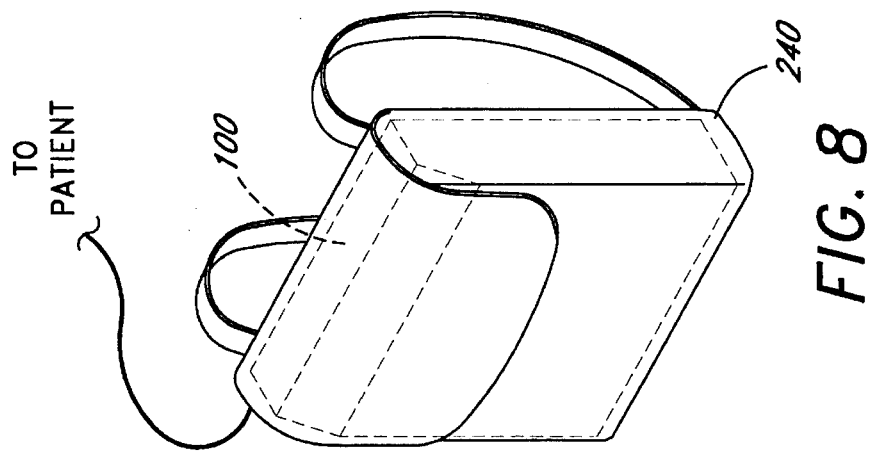
FIG. 8 is a diagram illustrating a possible ambulatory embodiment according to the present invention.

FIG. 8 illustrates an additional ambulatory embodiment with the system 100 in a pack 240 which can be carried on a patient's back. As explained above, the ambulatory embodiments do not include some components such as a display and a strip chart recorder in order to reduce the weight and the power compensation. The system 100 could also be divided into various components distributed in a vest or on a belt to be worn by the patient.

During operation, the system 100 continuously monitors the cardiac status of the patient 110 by means of the ECG front end 140, and, if used, the secondary sensors 170. The ECG front end 140 receives electrical signals which are sensed by the electrodes 143–145, and transmitted to the ECG front end 140 via the lines 146–148. The electrical pulses received by the ECG front end 140 represent the relaxation and contraction of the heart muscles, as is well understood in the art. During normal sinus rhythm, the heart muscles relax and contract in synchronization so that blood is pumped throughout the patient's body at a normal rate. However, if the patient 110 is experiencing a cardiac arrhythmia, the response of the heart to the signals produced by the auto-nervous system which regulate the beating of the heart becomes irregular. Irregular rhythms are typically represented by noticeably different electrical signals which are detected by the ECG front end 140. Thus, the electrical signals detected by the ECG front end 140 may be processed and analyzed to determine if the patient 110 is experiencing a cardiac arrhythmia.

The ECG front end 140 performs preliminary processing functions on the electrical impulses, and transmits this processed information to the signal conditioning circuitry 150 via the lines 152. The signal conditioning circuitry 150 performs additional filtering and processing functions on the impulses as determined by control signals transmitted from the microprocessor 120. The signal conditioning functions, as well as the preliminary processing functions, may be modified automatically by the microprocessor 120 to account for variations in the impulses due to the individual cardiac characteristics of each patient 110 (such as ECG amplitude). In such instances the microprocessor 120 may, for example, be used to control each of the programmable settings of the signal conditioning circuitry 150. For instance, the ECG signals are typically amplified to allow sampling. In one embodiment, advantageously, the gain is automatically varied by the system to generate ECG signals with appropriate amplitude for sampling.

The signal conditioning circuitry 150 transmits the conditioned impulses to the analog-to-digital converter 160 via the lines 162. The digitized impulses are then transferred to the microprocessor 120 where they are analyzed to determine the heart condition of the patient 110.

Functions performed by the ECG front end 140, the conditioning circuitry 160, and the microprocessor 120 are incorporated within a noise and artifact discrimination procedure. This procedure allows the system 100 to discriminate between the pulses which represent the actual rhythms of the patient's heart, and the erroneous signals produced by noise and artifacts which may be inherent within the system 100, or which may be produced by external sources. The system 100 effectively discriminates between pulses which represent the cardiac status of the patient and noise and artifact by means of both the hardware and the software employed within the system 100. In the hardware, the signals detected by the sensing electrodes 143, 144 and 145 are filtered so that frequencies above and below selected frequencies (e.g., in one embodiment below 1.5 Hz and above 40 Hz) are attenuated. Advantageously, the filtered frequencies are selected to significantly reduce low frequency baseline wander, low frequency motion artifacts, high frequency muscle noise, and 50/60 Hz power signal interference. In the software, the method employed to detect cardiac arrhythmias further attenuates muscle noise and motion artifacts. In addition to the measures used within the software and hardware of the system 100 to reduce noise and artifact and in order to increase the ability of the system 100 to discriminate between the true cardiac signals and the erroneous signals, one embodiment of the system 100 also incorporates the secondary sensors 170.

The secondary sensors 170 may have programmable features and are used for monitoring patient hemodynamics or other patient conditions to verify the accuracy of the ECG signals received by the system. As mentioned above, the secondary sensors 170 may include a blood oxygenation sensor and a cardiac microphone so that the blood oxygen level of the patient 110 and the audible rhythms of the patient's heart can be monitored, in addition to the electrical pulses representing the beating of the patient's heart. The secondary sensors 170 may also include signal processing and conditioning circuitry which act to reduce erroneous signals due to noise and artifact. Once the required processing of the signals received by the secondary sensors 170 has been performed, the data obtained from the secondary sensors 170 is transmitted to the microprocessor 120 where it is analyzed to determine the cardiac status of the patient 110. The noise and artifact discrimination procedure is described in greater detail below with reference to FIG. 4.

Once the microprocessor 120 has analyzed the data obtained from the electrodes 143–145 and the secondary sensors 170 (if utilized), a determination is made whether the received data indicates that the patient is in a nonshockable rhythm, or whether the patient is experiencing a shockable cardiac arrhythmia. The method employed in accordance with the present invention to make this determination is detailed below with reference to FIG. 5 and FIG. 6. The determination of the patient's cardiac status is made, in part, in response to the parameters which are input into the system 100 by means of the control and display panel 124 and/or the external programming unit 187. For instance, as depicted in FIG. 2, the control and display panel 124 includes the ventricular tachycardia (VT) rate cutoff control 217. The VT rate cutoff is discussed below. This parameter can be set via the VT rate cutoff control 217 on the control and display panel 124 or via the external programming unit 187. Of course, other programming means could be used such as initial programming of the microprocessor 120. These parameters are typically input by medical personnel who are familiar with the medical history of the patient 110 and the current diagnosis of the patient's condition. Similarly, the therapy administered in the case of the onset of an arrhythmia is controllable through the programming of the unit. This programming may be provided through the external programming unit 187 or through initial programming of the microprocessor 120. Thus, in accordance with their knowledge of the patient's condition, trained medical personnel are able to provide the proper inputs to the system 100 which serve to maximize the monitoring capability and the therapeutic effect of the system 100. Advantageously, these parameters are stored in the parameter memory 121.

In one embodiment, the system 100 includes additional programming features such as "batch processing." Batch processing allows a physician to set individual program settings into the external programming unit 187 and, after the program is satisfactory, download the program to the system 100 with a "one-stroke" command. This permits the attending physician to remove any programming errors before loading the parameters into the system 100.

The system 100 also includes a preset-yet-programmable-profile feature. This feature provides an assortment of preset program settings controlling arrhythmia detection and the therapy administration, and allows the physician to either modify existing profiles or to create new profiles in the form of individual program settings and to store them in the external programming unit 187 as a series of customized program settings that represent the most frequently encountered settings the physician may deem most universal. This feature allows the physician to quickly select the most appropriate parameters for a patient 110 and download the profile to the microprocessor 120 within the system 100. Furthermore, the preset-yet-programmable-profile feature allows the physician to quickly modify one or more of the individual settings in the profiles to simplify programming and to reduce programming time. This is particularly useful when a profile contains parameters which are very near those that the physician desires to apply in an individual patient's case, but requires a few changes to various parameters. The physician could simply select one of the preset profiles which is very close, and alter the desired parameters. This saves significant time over establishing new profiles each time the unit is used for a new patient.

Should the physician wish to establish an altered profile as a new profile for later use, the system 100 permits this capability without deleting the original profile which remains in permanent memory. The system 100 may have any number of preset profiles already resident in permanent memory. Advantageously, the preset profiles represent the most appropriate settings for a wide variety of patients, and the system 100 will accommodate as many additional profiles (subject to storage capacity) as the physician wishes to establish. In one embodiment, the system may display on command a listing of each of the established profiles resident in permanent memory along with each of their individual settings.

Once the appropriate parameters have been set by means of the control panel 124 and/or the external programming unit 187, and data relating to the condition of the particular patient 110 has been input into the system 100, the microprocessor 120 is able to make determinations relating to the cardiac condition of the patient 110. In accordance with these determinations, the microprocessor 120 transmits control signals to the cardioverter/defibrillator circuitry 130. The cardioverter/defibrillator circuitry 130 may be used to regulate the beating of the patient's heart if the patient 110 suffers from a cardiac arrhythmia. The patient 110 may, for example, suffer from a chronic arrhythmia which requires continuous regulation, or the patient 110 may simply be at risk of experiencing the sudden onset of ventricular fibrillation or ventricular tachycardia, so that only fibrillation or tachycardia corrective therapy is required.

In one embodiment, if the patient 110 suffers from one or more chronic arrhythmias, a low level electrical stimulus which compensates for the improper electrical impulses of the patient's heart may be applied by means of the delivery electrodes 133, 134. This low level electrical stimulus is similar to that provided by conventional pacemaker devices which act to pace the heartbeat of the patient 110. The amplitude and wave shape of the electrical stimulus is controllable by the cardioverter/defibrillator circuitry 130 in accordance with the control signals provided by the microprocessor 120 via the lines 132, and the settings and inputs provided during programming. In one embodiment, the microprocessor 120 adjusts the electrical stimulus in response to the inputs received from the ECG front end 140 and the secondary sensors 170, so that a feedback loop is established which allows the system 100 to better compensate for the chronic cardiac arrhythmia which is being treated. Thus, the system 100 may also provide a continuous cardiac monitoring and regulation device for the treatment of chronic arrhythmias.

If the patient 110 is at risk of the sudden onset of ventricular fibrillation, ventricular tachycardia, or other catastrophic cardiac arrhythmias, the system 100 continuously monitors the cardiac status of the patient 110. If an irregularity is detected in the patient's cardiac rhythm (e.g., irregular electrical impulses, a low blood oxygenation level, etc.), then the microprocessor 120 tests to determine if the irregularity constitutes the onset of ventricular fibrillation or ventricular tachycardia. In order to detect and distinguish between the types of cardiac arrhythmias (e.g., ventricular fibrillation or ventricular tachycardia), a procedure is used which takes into account the patient's heart rate and the morphology of the patient's ECG signal. The manner in which the detection and discrimination of the types of cardiac arrhythmias occurs will be described in greater detail with reference to the flowchart of FIGS. 5 and 6 below.

If ventricular fibrillation or ventricular tachycardia is detected, then the microprocessor 120 transmits a signal which causes the cardioverter/defibrillator circuitry 130 to administer one or more therapeutic electrical pulses via the delivery electrodes 133 and 134 to counteract the detected electrical instabilities. In one embodiment, signals representing the administered electrical pulses may be visually displayed on the optional display 137. The administered electrical shocks may vary in intensity and frequency depending upon the nature of the detected arrhythmia and the programmable parameters of the system. In addition, the shocks may be delivered synchronously (for ventricular tachycardia) or asynchronously (for ventricular fibrillation and related arrhythmias) relative to the patient's QRS complex. A detailed description of the method used to effect cardioversion in accordance with the present invention is provided with reference to FIGS. 3A–3C below.

In addition to providing monitoring and electrical cardiac regulation, one embodiment of the system 100 of the present invention is capable of communicating with a physician or other trained medical personnel from a remote location. This may be accomplished by means of the bidirectional communication link 180. In one embodiment, wherein the system 100 is embodied as a bedside unit, the bidirectional communication link 180 may be implemented as a telephone modem device. In another embodiment, wherein the system 100 is embodied as an ambulatory monitor and cardioverter/defibrillator device, the bidirectional communication link may be implemented as a two-way communications radio, or other device which is capable of transmitting and receiving radio signals.

The bidirectional communication link 180 is advantageously able to transmit and receive information relevant to the treatment of the patient 110. In one embodiment, the bidirectional communication link 180 transmits patient information to the corresponding doctor's office or hospital for evaluation and analysis. In addition, the link 180 transmits real time ECG data to verify proper acquisition of the signals, and proper attachment of the sensing electrodes 143–145. The ECG signals aid the doctor in evaluating the patient's condition without requiring the patient 110 to travel to the hospital. Other useful information that may be transmitted includes the status of the system 100 itself in case any system malfunctions are observed, so that the physician is able to make a recommendation to correct the situation. Furthermore, the bidirectional communication link 180 can receive information from a remote location such as a doctor's office or hospital. In this embodiment, the microprocessor 120 may be externally programmed through the bidirectional communication link 180.

In order to externally program and monitor the system 100, the external programming and monitoring unit 187 may be employed at the hospital end of the bidirectional communication link 180. For example, a personal computer or custom computer designed for this task may be employed as the external programming and monitoring unit 187. By means of this external programming and monitoring unit 187, a physician or other trained medical personnel can program a wide range of programmable functions into the microprocessor 120. The physician may, for example, alter parameters such as the VT rate cutoff (i.e., the heart rate above which ventricular tachycardia is detected), the delay times before selected therapeutic electrical pulses are delivered, the energy levels at which selected shocks are to be administered, and in one embodiment, patient warning signals. In addition, the physician may set or alter such parameters as pulse delivery manual override (i.e., manual override by the operator of delivery of therapy or manually initiating therapy), and the pulse delivery rate (i.e., the rate at which therapeutic electrical pulses are administered to the patient). These functions and others will be explained in greater detail below. It should be noted that the external programming unit 187 may also be incorporated within the control and display unit 124, or as an additional host computer system which may be coupled to the microprocessor 120. Finally, the data which may be monitored through the external programming and monitoring unit 187 can be transferred to other data storage devices including magnetic or hard data storage peripheral devices, a printer, the strip chart recorder 129, or other similar data recording means.

Figure 3A:
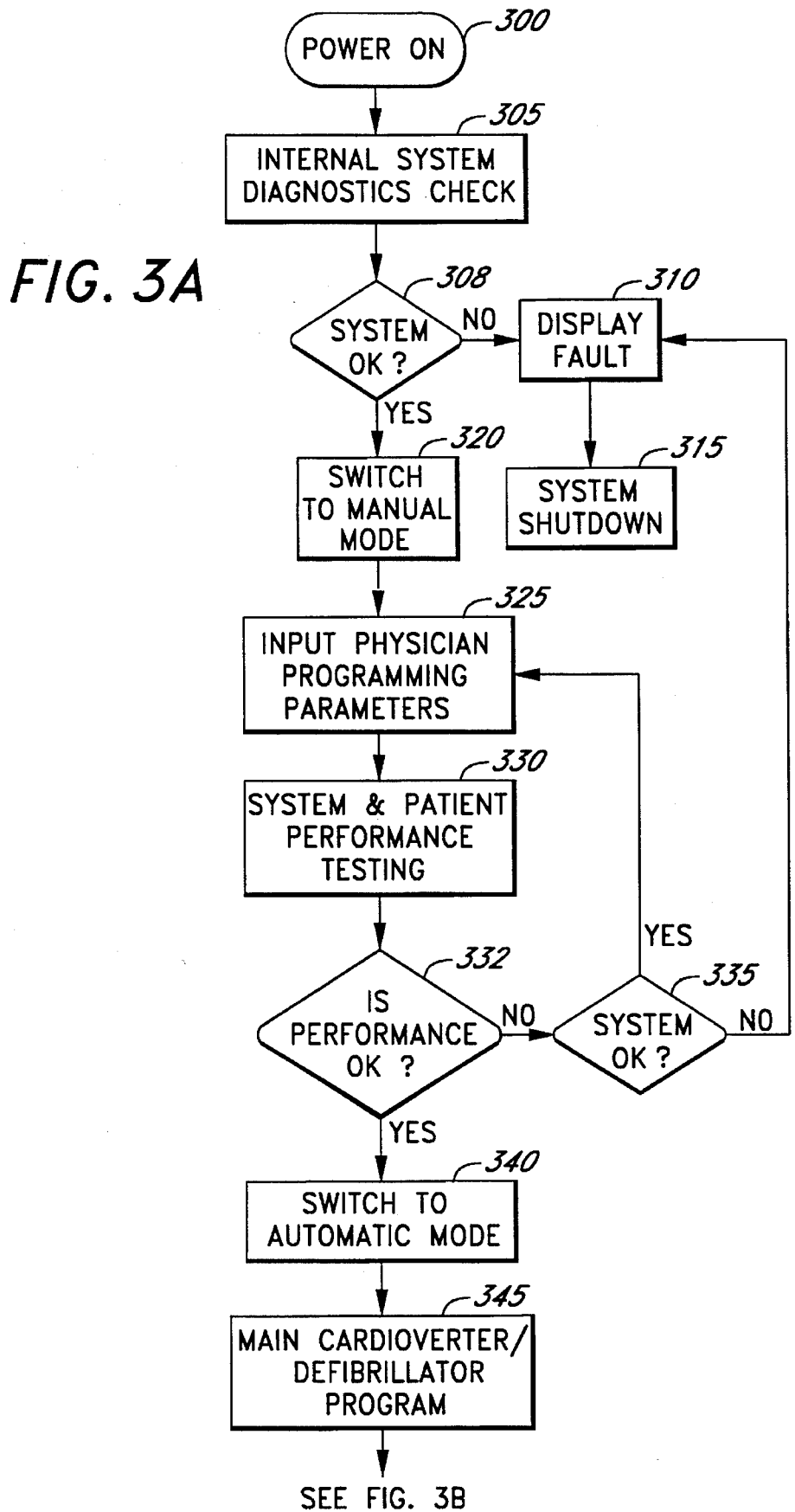
FIGS. 3A, 3B, and 3C are flowcharts which detail the overall method of operation employed in accordance with the invention.
Figure 3B:
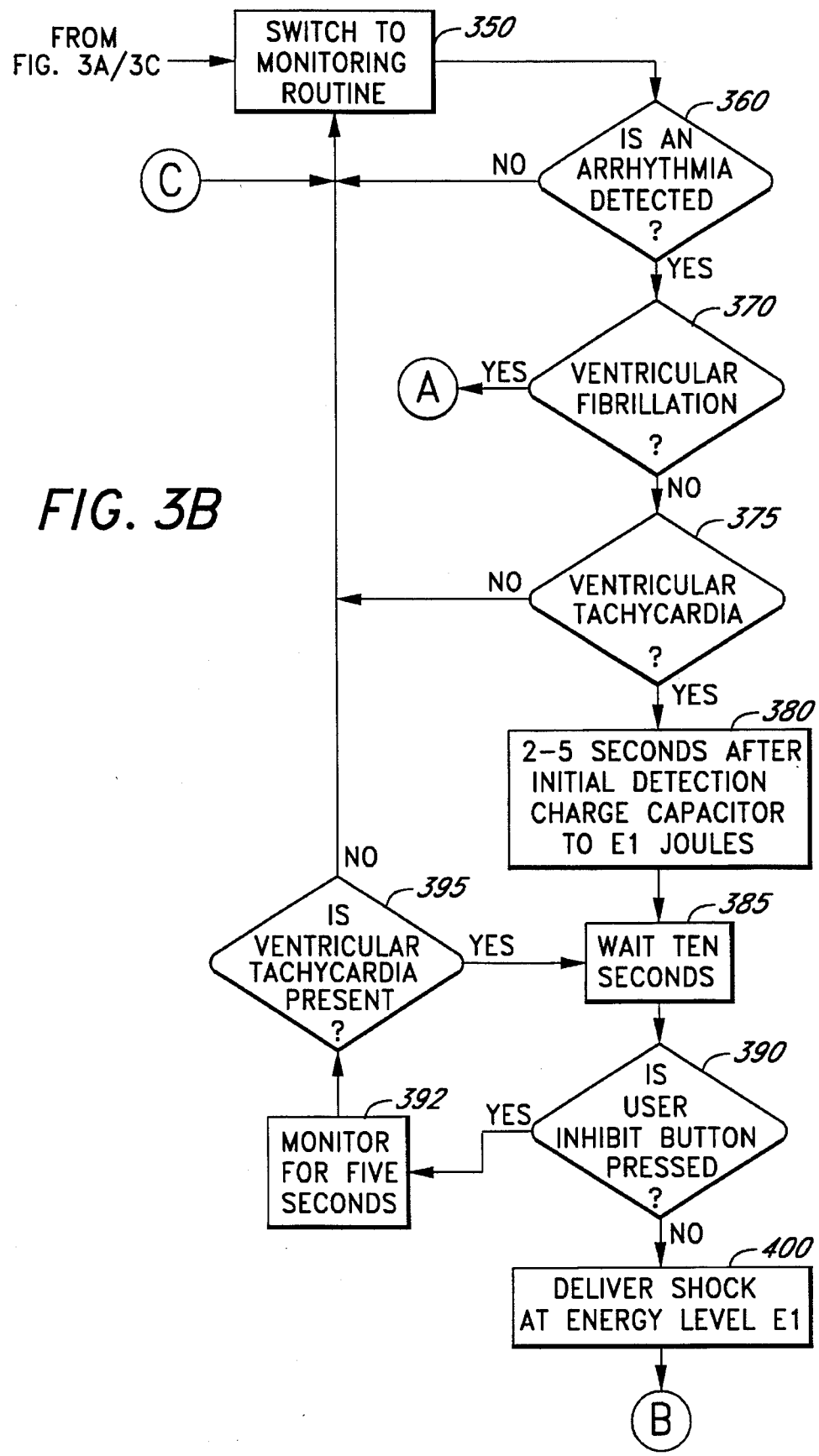
Figure 3C:
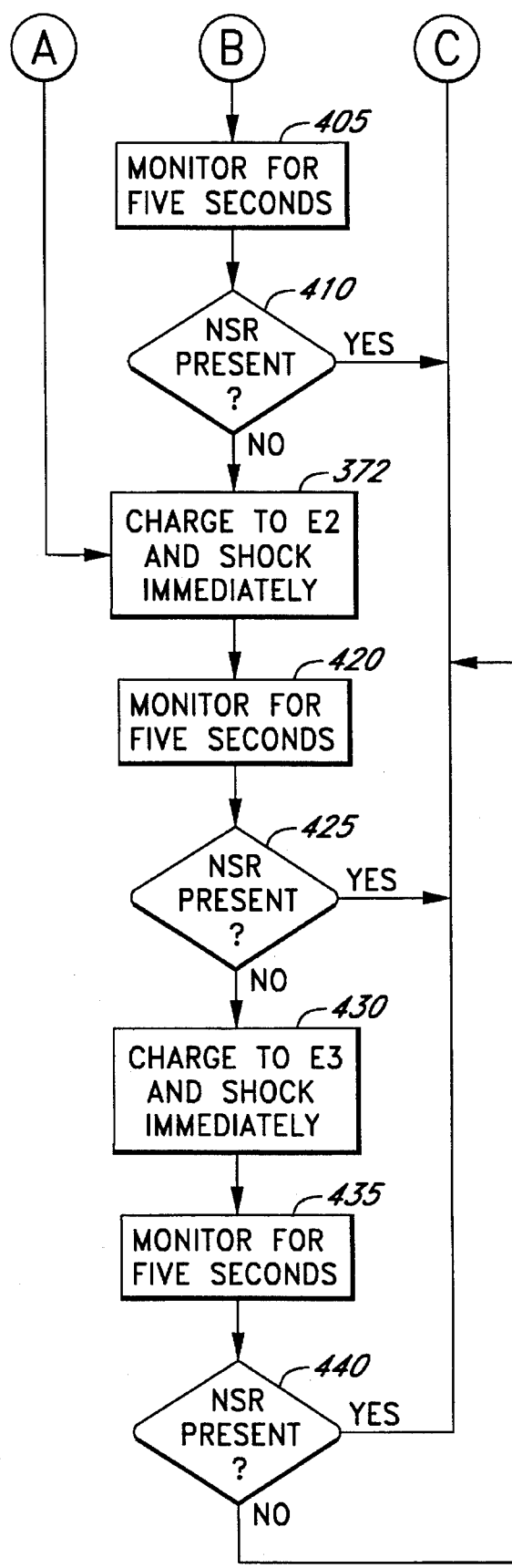
Figure 3C:
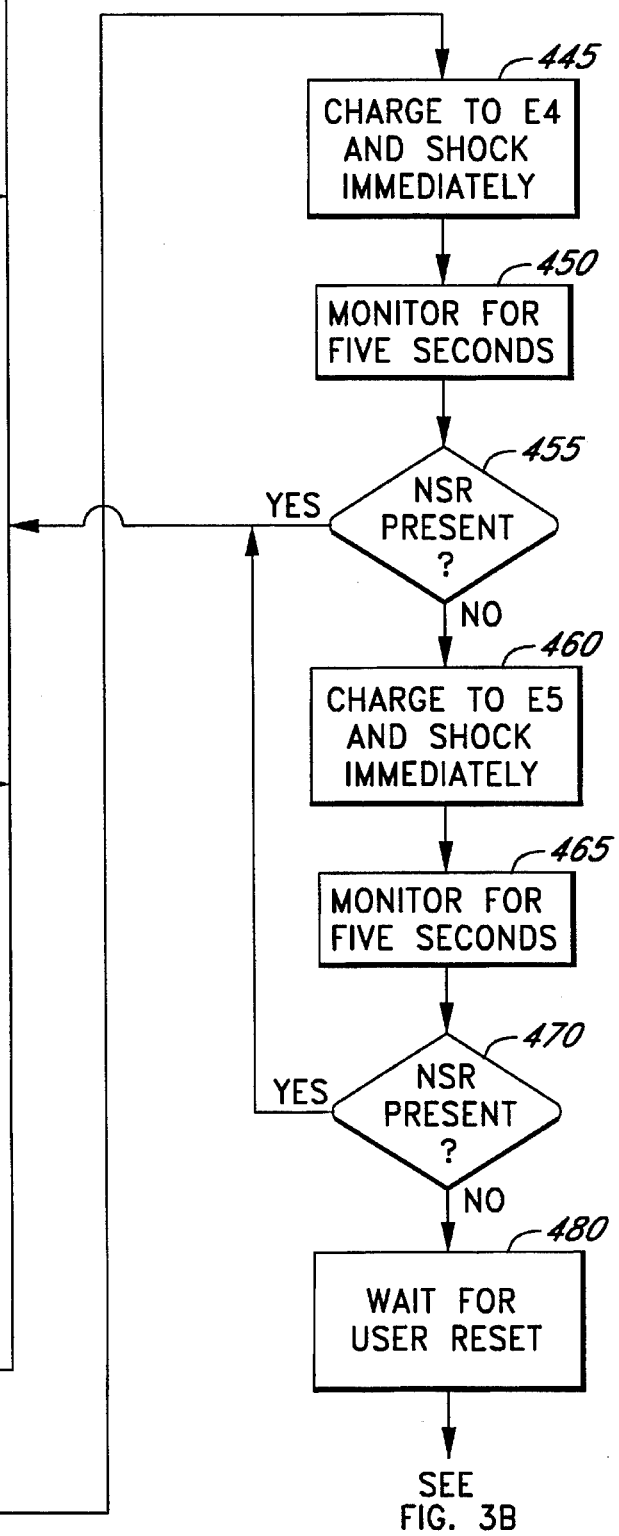

The overall method employed by the system 100 for monitoring and cardioverting and/or defibrillating the patient 110 is described with reference to the flowchart of FIGS. 3A–3C. As shown in FIG. 3A, once the power is supplied to the system 100 in a start block 300, an internal system diagnostics check is performed in a process block 305. The internal diagnostics execute system checks on functions such as battery life (for units configured with batteries), the status of the charging capacitor within the cardioverter/defibrillator circuitry 130, the sensing electronics, the charge and discharge circuitry within the cardioverter/defibrillator circuitry 130, and the status of the electrodes 143–145. In one embodiment, the system diagnostics also detect the patient impedance between the delivery electrodes 133, 134, and automatically adjust the voltage applied across the delivery electrodes in order to deliver the desired electrical therapy power to the patient 110 based upon this impedance (e.g., a higher impedance requires a higher voltage).

After the diagnostics check has been performed, control passes to a decision block 308 wherein a determination is made if the functions of the system 100 are working properly. If the diagnostics check determines that one or more of the functions of the system 100 are not in proper order (for example, if one or more of the sensing electrodes 143–145 or the delivery electrodes 133, 134 has become loose or disconnected), then control passes to a display fault block 310 wherein a warning message is communicated to the patient 110 by means of any combination of audible, tactile, visual or other discernible signal. Control then passes to a system shutdown block 315, wherein all functions of the system are suspended until the malfunctions within the system 100 have been corrected. If, however, no malfunctions are found within the system 100 by the internal diagnostics check, control passes from the decision block 308 to a process block 320.

In the process block 320, the operation of the system 100 is switched to the manual mode. Once in this mode, control passes to a process block 325 which allows a physician or other operator to manually set system parameters and to select certain system functions. This is advantageously done by means of the control and display unit 124, or through the bidirectional communication link 180. As discussed above, the physician may program macros or employ the preset profiles of the system 100 to tailor the input parameters to the individual patient 110. The parameters which are set may include any of the programmable system parameters such as those used to evaluate arrhythmias and those used to control the electrical therapy. Control then passes from the process block 325 to a system and patient performance testing process block 330.

In the system and patient performance testing block 330, the system operator (e.g., a doctor or other trained medical professional) may observe the patient's ECG via the control and display unit 124, or optionally through the external ECG monitor 137. This allows the operator to determine if the system is properly monitoring the patient. In this mode, the operator is able to test the system 100, as well as perform electrophysiological studies on the patient 110. Further diagnostics and testing may be accomplished by means of the external programming and monitoring unit 187. Thus, the physician will be able to test the system 100 to verify proper operation and response prior to releasing the patient 110 from the hospital, or as a regular system maintenance procedure which may be done from the hospital through the communication link 180.

Once the system and patient performance testing has been done, control passes to a decision block 332, wherein a determination is made if the performance of the system 100 is normal. If the system performance is not normal, then control passes to a decision block 335, wherein a determination is made if the system 100 has malfunctioned. If the system 100 is not functioning properly, then control passes to the display fault block 310, and from there passes to the block 315 wherein the system 100 is shut down. If however, there is no permanent malfunction found in the system 100, then control once again passes to the process block 325, and from there to the process block 330 so that the performance of the system 100 can once again be tested. Control then returns to the decision block 332 wherein a new determination is made if the system performance is normal.

Once the performance of the system 100 is determined to be normal, control passes to a process block 340, wherein the system 100 is switched to the automatic mode so that automatic control and monitoring functions can be performed. Control then passes to a process block 345, wherein the main cardioverter/defibrillator program is initiated. Once the main cardioverter/defibrillator program has been initiated, the system begins the monitoring routine within a process block 350. When the system 100 begins the monitoring routine, a monitoring subroutine is initiated which acts to monitor the cardiac status of the patient 110 by means of the ECG front end 140, and possibly, the secondary sensors 170.

The general procedure followed during the monitoring subroutine comprises the steps of detecting an arrhythmia, determining if the arrhythmia corresponds to ventricular fibrillation or ventricular tachycardia, and taking the appropriate measures to counter the detected arrhythmia. At the beginning of the monitoring subroutine, control of the main cardioverter/defibrillator program is transferred from the process block 350, to a decision block 360, wherein a determination is made if a cardiac arrhythmia is detected. The determination of whether or not a cardiac arrhythmia is detected and the determination of which type of arrhythmia is present are dependent upon conditions and preset parameters which are described in detail with reference to a detection procedure described with reference to FIGS. 5 and 6 below.

If no arrhythmia is detected within the decision block 360, control returns to the process block 350, where the monitoring routine is re-initiated. If an arrhythmia is detected, however, control passes from the decision block 360 to a decision block 370 wherein a determination is made if the detected arrhythmia is a ventricular fibrillation. Since ventricular fibrillation is a more severe cardiac arrhythmia, immediate and intense therapeutic measures should be taken if ventricular fibrillation is detected. Thus, if the arrhythmia is determined to be a form of ventricular fibrillation, then control passes immediately to a process block 372 (FIG. 3C, through a continuation point A) wherein the proper components within the cardioverter/defibrillator circuitry 130 are charged to a programmable energy level E2 (e.g., 40 to 360 joules for ventricular fibrillation therapy), and an electrical shock is immediately administered to the patient 110 by means of the paddles 133, 134. This electrical shock is typically administered asynchronously with the patient's ECG rhythm. The energy level E2 was programmed into the system as a parameter during process block 325.

If the detected arrhythmia is not determined to be a form of ventricular fibrillation, then control passes to a decision block 375 (FIG. 3B), wherein a determination is made if the detected arrhythmia is a form of ventricular tachycardia. If ventricular tachycardia is not detected, control returns to the process block 350 so that the monitoring routine can be re-initiated. If ventricular tachycardia is detected, then control passes to a process block 380, wherein a selected programmable delay (e.g., 2–5 seconds in the present embodiment) is observed prior to the charging of the capacitor within the cardioverter/defibrillator circuitry 130. Then, the capacitor is charged to a programmable energy level of E1 (e.g., 15 joules, for example). The duration in time of delivery of any single therapeutic cardioverting/defibrillating energy (i.e., the period of time required to deliver a single cardioverting/defibrillating shock) is well defined in the art. As with E2, E1 was programmed into the system during the programming represented in the process block 325. Control then passes to a process block 385, wherein a second selected programmable delay (e.g., ten seconds in the present embodiment) is observed. In embodiments which include a signalling device which signals to the patient that therapy is about to be initiated, a signal could be provided to the patient a few seconds before therapy is administered. This function is not depicted in the flowchart of FIGS. 3A–3C. Control then passes to a decision block 390, which determines if the user inhibit button 188 is depressed.

If the user inhibit button is depressed, this indicates that the patient 110 does not believe that electrical therapy is necessary. In this case, control passes to a process block 392, wherein the patient's condition is monitored once more for a selected programmable duration (e.g., 5 seconds). Control then passes from the process block 392 to a decision block 395 wherein a determination is made if ventricular tachycardia is still present. If ventricular tachycardia is not detected, control returns to the process block 350 so that the monitoring routine can be re-initiated. If ventricular tachycardia is still detected, then control returns to the process block 385, wherein another selected programmable delay (e.g., ten seconds) is observed. Control then returns to the decision block 390 to determine if the user inhibit button 188 is depressed. This cycle continues until ventricular tachycardia is no longer detected, or until the patient 110 is no longer depressing the user inhibit button 188, or a programmable number of times, after which the device could be programmed to deliver therapy regardless of the state of the user inhibit switch.

If ventricular tachycardia is detected, and the user inhibit button 188 is not depressed, then control passes to a process block 400, wherein an electrical shock having an energy level E1 (e.g., 15 joules) is delivered to the patient 110. For ventricular tachycardia, this electrical pulse is delivered synchronously with the 'R' wave of the QRS complex (i.e., a finite time after the detection of the peak of the 'R' wave). Once the electrical shock is administered to the patient 110, control passes to a process block 405 (FIG. 3C, through a continuation point B) wherein the patient's cardiac status is monitored for a selected programmable period (e.g., five seconds in the present embodiment). Control then passes to a decision block 410 wherein a determination is made whether the patient's heart has resumed a non-shockable rhythm (NSR) such as normal sinus rhythm. If a non-shockable rhythm is present, then control passes to the block 350 (FIG. 3A, via the continuation point C) where the monitoring routine is re-initiated. If a non-shockable rhythm is not present, further programmed therapy should be delivered, and control passes to the process block 372.

As discussed above, the process block 372 is also entered immediately when the more serious condition of ventricular fibrillation is detected. In addition, the process block 372 is entered when the initial shock delivered at the energy level E1 is unsuccessful to convert a patient suffering from tachycardia to a non-shockable rhythm. When the process block 372 is entered, the capacitor within cardioverter/ defibrillator circuitry 130 is charged to the programmable energy level E2. As noted above, this energy level is generally higher for a patient suffering from ventricular fibrillation than for a patient suffering from ventricular tachycardia. Thus, as an example only, the energy level E2 may be 40 joules if ventricular fibrillation is detected, or 25 joules if ventricular tachycardia is present. In addition, the electrical pulses administered to correct ventricular tachycardia are typically synchronous with the 'R' wave of the QRS complex, while the pulses used to correct ventricular fibrillation are not administered synchronously with the patient's QRS complex. When the appropriate circuitry within the cardioverter/defibrillator circuitry 130 is charged to the energy level E2, an electrical shock is immediately delivered to the patient 110.

Control then passes to a process block 420, wherein the cardiac status of the patient 110 is monitored for another predetermined programmable period (e.g., five seconds in the present embodiment). Control then passes to a decision block 425, wherein a determination is made if an NSR is present. If an NSR is present, this indicates that the shock delivered at the energy level E2 was successful and control returns to the control block 350 (FIG. 3B) to once again initiate the monitoring routine. If an NSR is not present, then control passes to a process block 430 (FIG. 3C), wherein an electrical charge at the energy level E3 (e.g., 100 joules for fibrillation, and 35 joules for tachycardia) is delivered to the patient 110. The patient 110 is once again monitored for a programmable period (e.g., five seconds) in a process block 435, and a determination is made if an NSR is present in a decision block 440. If an NSR is not achieved, this pattern continues until an NSR is restored. Therefore, therapy at programmable energy levels E4 (e.g., 150 joules for fibrillation, and 45 joules for tachycardia), and E5 (e.g., 200 joules for fibrillation, and 55 joules for tachycardia) may also be delivered within the process blocks 445 and 460, respectively. Likewise, between each delivery of therapy, monitoring is performed for a predetermined programmable period (e.g., a five second duration) in the process blocks 450 and 465, and a determination is made if NSR has been restored in the decision blocks 455 and 470. If NSR has not been restored after delivery of energy E5, the defibrillation process waits for an operator reset in process block 480, after which all sequence counters are reset and the patient is monitored beginning at process block 350.

It should be noted that the number of energy levels for cardioversion and/or defibrillation may be varied via the programmable parameters, as well as the total number of energy level. The levels described above are, therefore, merely exemplary. The energy levels E1–E5 may also be varied significantly depending upon factors such as the patient impedance, the type of arrhythmia detected (i.e., ventricular fibrillation or ventricular tachycardia), the cardiac history of the patient 110, and the type of system which is employed. For example, if the bedside model of the system 100 is employed rather than the portable model of the system 100, then the energy levels E1–E5 may be, for example, 15 joules, 40 joules, 120 joules, 240 joules, and 360 joules respectively. Similarly, if the patient is suffering from ventricular tachycardia rather than ventricular fibrillation, then the energy levels of the administered electrical pulses may be lower than those employed to defibrillate the patient 110. It should be noted that the energy levels listed in this description are merely exemplary and would be appropriately selected by the attending physician, depending upon the particular patient and conditions involved. Similarly, although default values may be programmed into the system, the delays listed above would advantageously be selected by the attending physician, depending upon the patient and the condition. This therapy routine (i.e., continually increasing the energy level delivered until cardioversion or defibrillation occurs or a maximum energy level is reached) is hereafter referred to as "step therapy."

As mentioned previously, it is important for the system 100 to discriminate properly between noise and artifact signals and the actual electrical pulses which represent the cardiac rhythms of the patient 110. If this is not accomplished properly, it is possible that the system 100 will deliver a cardioverting or defibrillating shock in an unwarranted situation. This could possibly initiate a cardiac arrhythmia in the patient 110. In the event that erroneous therapy is administered to the patient 110 which results in the onset of cardiac arrhythmia, the operations of the system 100 will recycle to command the cardioverter/defibrillator circuitry 130 to defibrillate the patient 100 so that an NSR is restored.

Figure 4:
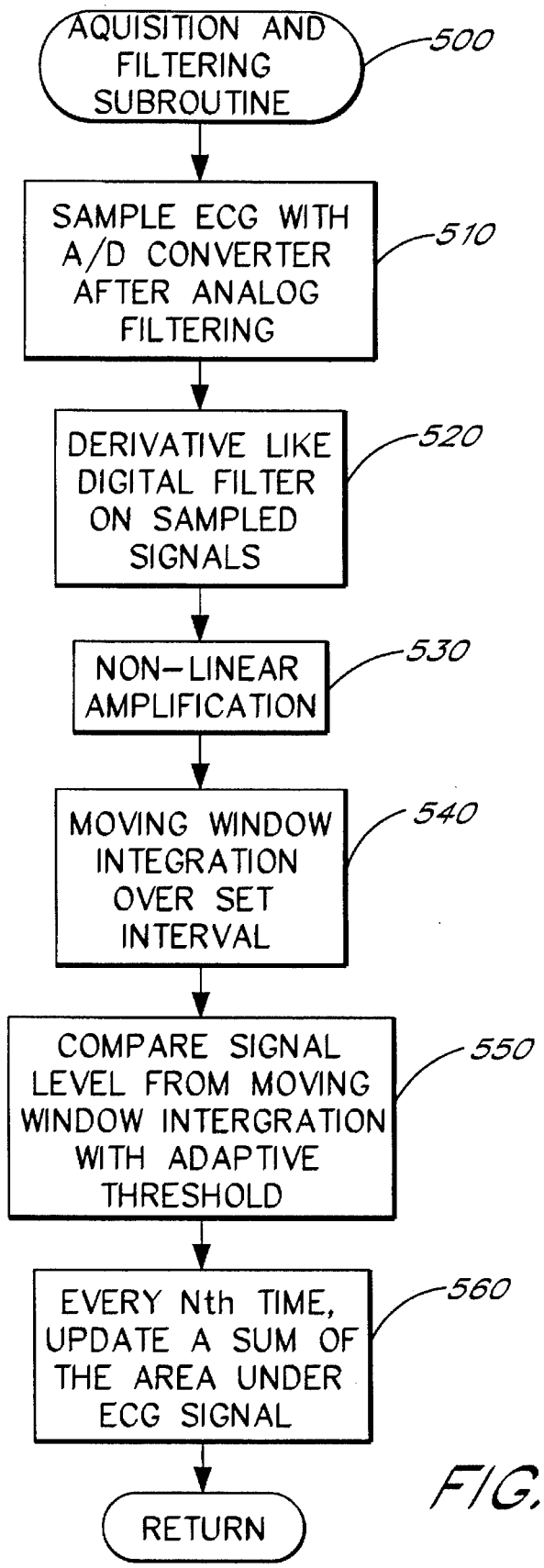
FIG. 4 is a flowchart which details a method of noise and artifact discrimination employed by a subroutine in the flowchart of FIGS. 3A, 3B and 3C.

FIG. 4 is a flowchart which details a method employed by the system 100 to discriminate between the signals representing the cardiac rhythms of the patient 110 and noise and artifact signals. The method begins in a start block 500, and proceeds to a process block 510, wherein the ECG signal is digitally sampled. It should be noted that the ECG signal is typically analog filtered by means of the system hardware prior to the digital sampling performed in the process block 510. Once the signal has been digitally sampled, control passes to a process block 520, wherein a derivative or similar function is performed using the sampled signal. In an ECG signal, such as that expected at the output of the process block 510, the QRS component usually has the highest frequency. Thus, by taking the derivative or similar function using the sampled signal to obtain information about the slope of the QRS component, the QRS component of the ECG signal may be more clearly distinguished. Once the derivative or similar function has been performed using the sampled signal, control passes to a process block 530, wherein a non-linear amplification is performed on the differentiated (or similar) signal (i.e., the signal resulting from the process block 520). This amplification significantly increases the magnitudes of those samples which have high frequency values, while amplifying samples having relatively low frequency values to a significantly lesser degree. Once the signal has been amplified, control passes to a process block 540, wherein a moving-window integration of the amplified signal is performed. This moving-window integration is accomplished by summing each of the samples within a constant interval (e.g., an interval of ten samples), storing the total value, shifting the interval over one or more samples, and summing each of the values within the shifted interval. This process is repeated on a continuous basis so that a series of integration values is obtained. Process blocks 520–540 comprise a digital filter.

The signal comprising the integration values is compared with an adaptive threshold level in a process block 550. This adaptive threshold level may be set as the average of a predetermined number of previous detected QRS complexes. When the integration value signal exceeds the adaptive threshold level, this indicates that a QRS complex has been detected. When a QRS complex is detected, the system then examines the past ECG signal to locate the maximum of the signal in reference to the baseline of the patient's ECG signal (the ECG baseline being well known in the art). The maximum deflection is then selected as the peak of the R wave of the QRS complex.

Once the moving-window integration value has been compared to the threshold value to determine the location of the R-wave peaks, control passes to a process block 560, wherein the originally sampled ECG signal (i.e., the signal provided as the output from the process block 510) is processed to obtain the area between the detected ECG waveform and a patient baseline over a set time interval. The measured area is provided as a second signal which is indicative of the ECG waveform morphology. In normal sinus rhythm, the QRS pulses are very sharp, and enclose very little area. During ventricular fibrillation, however, the ECG flutters somewhat sinusoidally above and below the patient baseline, so that a significantly larger area is typically measured as the area between the ECG signal and the baseline. Consequently, if the area under the ECG waveform (i.e., between the ECG signal and the baseline) is above a certain morphology threshold, then this may be indicative of the onset of ventricular fibrillation. Thus, the area between the ECG and the baseline may be employed later as a means of detecting ventricular fibrillation. The system 100 therefore provides an accurate determination of the location and number of QRS complexes produced by the patient's cardiac rhythm, as well as a signal which is indicative of the ECG waveform morphology.

Figure 5:
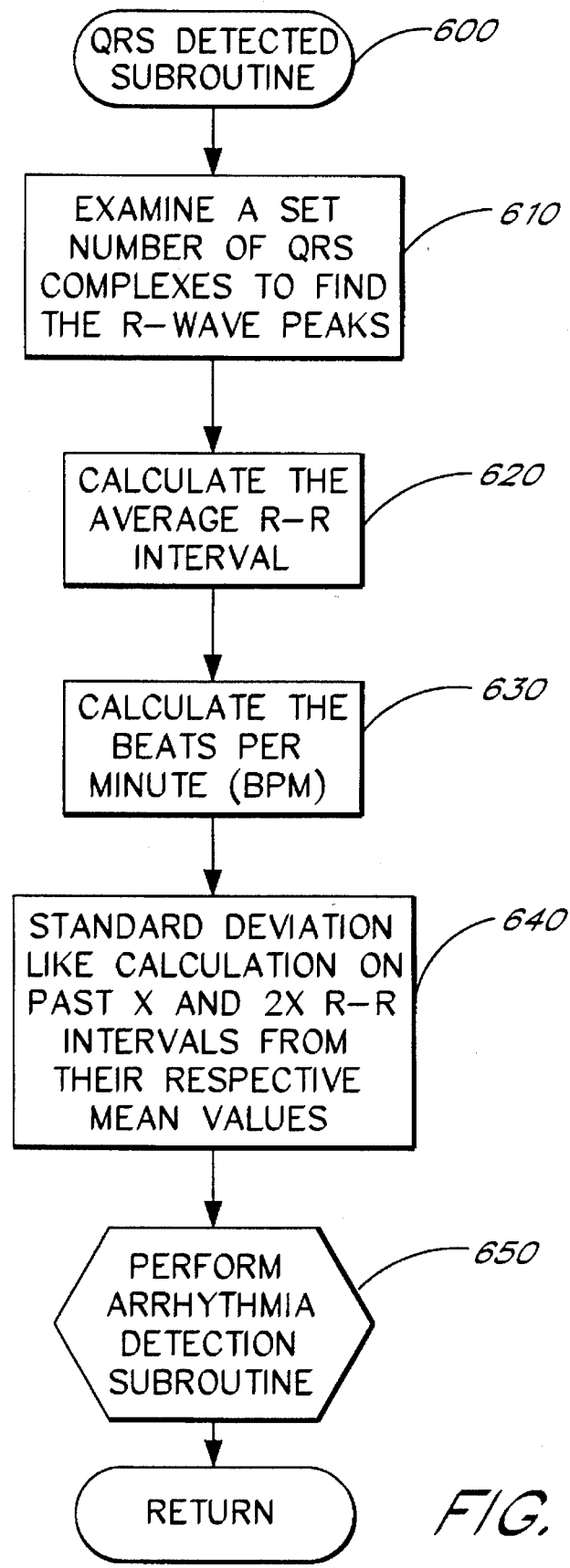
FIG. 5 is a flowchart which details the method employed in accordance with the present invention to analyze cardiac rhythms.
Figure 6A:
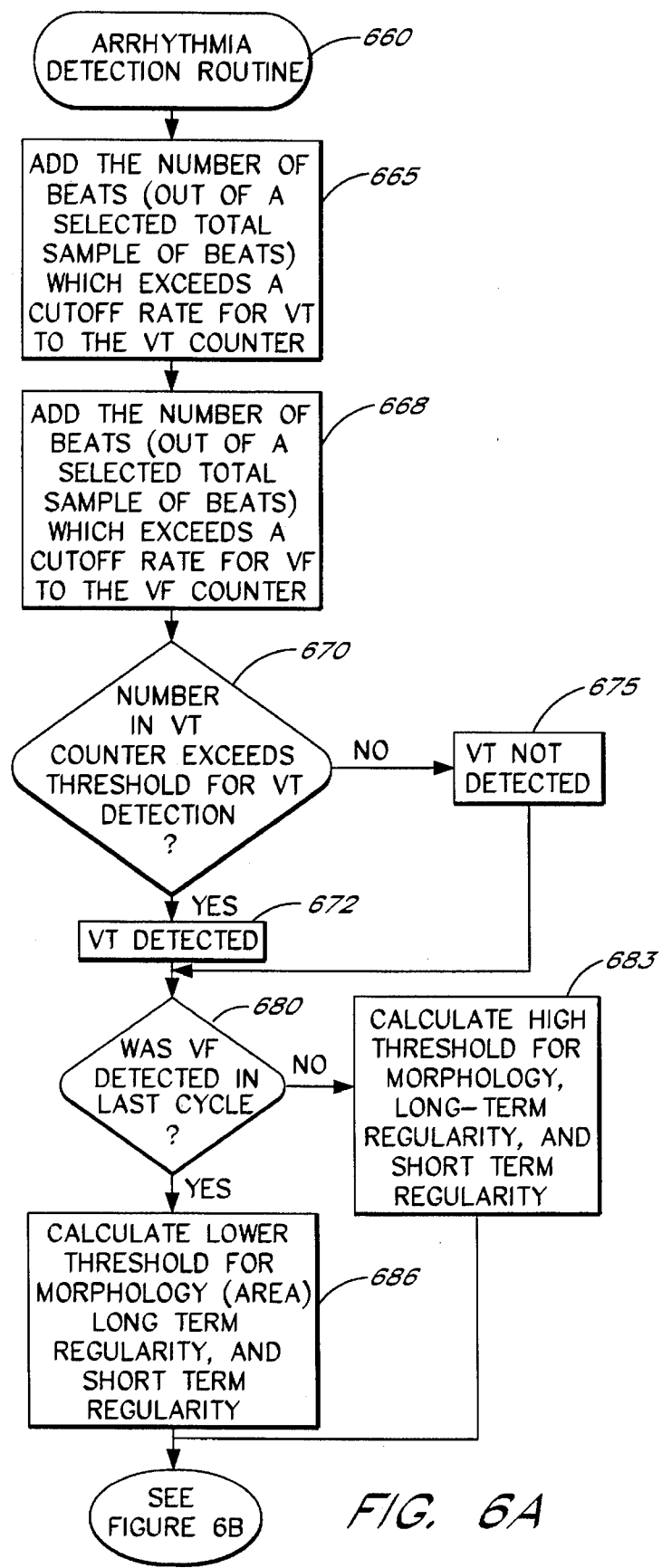
FIGS. 6A and 6B are flowcharts which show the details of an arrhythmia detection subroutine wherein the signals derived from the patient's ECG signal are analyzed to determine the type of arrhythmia present.
Figure 6B:
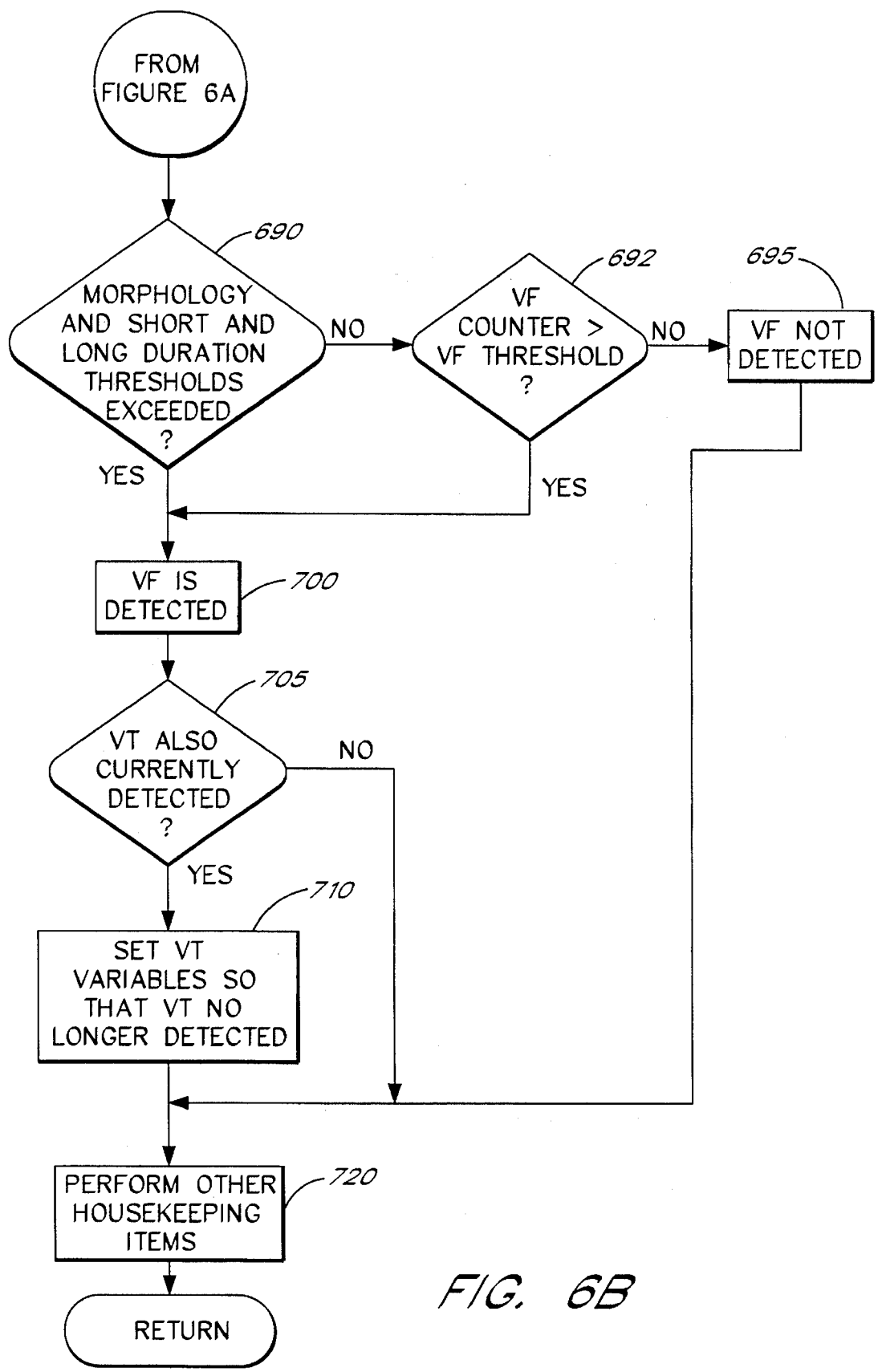

When the appropriate data have been acquired and filtered, the system 100 employs a method to determine if an arrhythmia is detected. FIGS. 5 and 6 are flowcharts which detail the method used by the system 100 to detect and distinguish between the types of cardiac arrhythmias. The method begins in a start block 600, and control passes to a process block 610, wherein a number of past QRS complexes are analyzed to find the peak of the R wave. This is advantageously accomplished by means of the procedure outlined above with reference to FIG. 4 wherein, when a QRS complex is detected, the ECG signal is examined to determine the maximum of the signal with reference to the patient baseline. The maximum deflection of the signal is the peak of the R wave. Control then passes to a process block 620, wherein the average interval between a set number (e.g., typically 10–30) of detected R-wave peaks is calculated. After the average interval between the R-wave peaks is calculated, this information is employed within a process block 630 to determine the number of beats per minute of the patient's heart.

Once the patient's heart rate has been determined, control passes to a process block 640, wherein a standard deviation like calculation is performed to determine the standard deviation of the time between heart beats. If the patient's heart beat is regular, then the standard deviation from the mean interval between beats will be very close to zero. If the patient's heart rate is grossly irregular, then the time interval between heart beats will be substantially random, and the standard deviation will be significantly higher. This standard deviation is advantageously calculated first over a relatively brief period, (e.g., three seconds, hereafter "short term regularity"), and a second time over a longer duration (e.g., six or more seconds, hereinafter "long term regularity"). Advantageously, the short term regularity interval is half of the long term duration interval. This is illustrated in the flowchart in process block 640 as a calculation on the past X and 2×R—R intervals. However, these durations need not necessarily be related in terms of one interval being twice the other interval. These parameters are advantageously programmable.

The values obtained from the calculations performed in the process block 640 aid in detecting ventricular fibrillation, since the heart beat pattern for persons suffering this type of arrhythmia is substantially random. Thus, a very high standard deviation value is indicative of the onset of ventricular fibrillation. The long duration standard deviation value (long term regularity) is used to determine if the onset of ventricular fibrillation has occurred, while the short duration standard deviation value is typically employed to determine if the patient has resumed a normal sinus rhythm after the administration of electrical therapy.

Once these values have been determined, control passes to a subroutine block 650 wherein the signals derived from the patient's ECG signal are analyzed to determine the type of arrhythmia, if any, the patient is suffering. The subroutine block 650 is described in detail with reference to FIGS. 6A and 6B. The arrhythmia detection subroutine shown in FIG. 6A begins in a start block 660, and control proceeds to a process block 665, wherein the number of beats which have occurred within a preset VT cutoff time after the previous beat is added to the value in a ventricular tachycardia (VT) counter. That is, a ventricular tachycardia (VT) cutoff time (e.g., ⅓ of a second) is programmed into the system 100, and this time is compared to the time intervals measured between the R peaks of successive heart beats. When successive beats are too close together (i.e., less than the cutoff time interval), this is indicative of the presence of a highly accelerated heart rate which is characteristic of ventricular tachycardia (and in some cases ventricular fibrillation). In the process block 665, a set number of beats, 20 for example, are analyzed to determine how many of the monitored heart beats have occurred within the VT cutoff time of the preceding beat. Those beats which are detected to be within the cutoff time of the preceding beat are added to a VT counter so that a total number of excessively fast beats within the monitored number is obtained. Thus, out of the monitored beats, a certain number of beats are detected to be too close to their preceding beats.

Once this is accomplished in the process block 665, control passes to a process block 668, wherein a procedure similar to that used in the process block 665 is employed to monitor for heart rates that are more specifically associated with ventricular fibrillation. In the process block 668, a separate ventricular fibrillation (VF) counter is employed, and a somewhat shorter programmable time interval (e.g., ¼ of a second) is used as the ventricular fibrillation (VF) cutoff value.

Once the number of beats which are excessively close to one another, as measured by both the ventricular tachycardia (VT) cutoff interval and the ventricular fibrillation (VF) cutoff interval, have been accounted for in the process blocks 665 and 668, control then passes to a decision block 670. In the decision block 670, a test is performed to determine if the number of beats in the ventricular tachycardia (VT) counter is in excess of a programmable ventricular tachycardia (VT) threshold value (e.g., 10). If the number stored within the ventricular tachycardia counter is in excess of this VT threshold value, this indicates that a high number of heart beats has been detected in close succession, and control passes to a process block 672, wherein an indication is made and stored in the microprocessor 120 that ventricular tachycardia is detected. If the value in the ventricular tachycardia counter does not exceed the set threshold value, then control passes to a process block 675, wherein an indication is made and stored that ventricular tachycardia is not present.

Control then passes to a decision block 680, wherein a test is performed to determine if, when the last cycle of the detection procedure was completed, the patient suffered from ventricular fibrillation (VF). If ventricular fibrillation was present at the end of the last cycle, then this indicates that the patient may still be suffering from ventricular fibrillation. Control therefore passes to a process block 686. Within the process block 686, low threshold values for morphology are calculated from parameters (which advantageously are programmable) for the area under the ECG (between the ECG and baseline), and the long and short duration standard deviations in the time difference between heart beats (long term and short term regularities) are calculated. The low threshold values are employed so that a less stringent requirement is met in order to continue to indicate the detection of ventricular fibrillation, since the previous test in the decision block 680 indicated that ventricular fibrillation is present. If, however, the test performed in the decision block 680 indicates that ventricular fibrillation was not present at the time of completion of the last monitoring cycle, then control passes to a process block 683, wherein higher threshold values for morphology are calculated for the area between the ECG and the baseline, and the long and short duration standard deviations in the time difference between heart beats (i.e., long term and short term regularity). The high threshold values are employed to insure that a more stringent requirement is met before the detection of ventricular fibrillation is signaled, since the previous test in the decision block 680 indicated that ventricular fibrillation was not present.

Once the appropriate threshold values have been set for the area between the ECG and the baseline, and the long and short duration standard deviation values, control passes to decision blocks 690 and 692 (FIG. 6B), wherein a determination is made if each of the morphology and long and short duration regularity thresholds have been exceeded, or if the number of beats stored within the ventricular fibrillation (VF) counter (i.e., the counter which was incremented in the process block 668) has exceeded a preset threshold value. If all of the appropriate thresholds have not been exceeded, and if the number of beats accumulated within the ventricular fibrillation counter does not exceed the VF threshold value, then control passes to a process block 695 wherein an indication is made that ventricular fibrillation is not detected, and, subsequently, control passes directly to a process block 720. If, however, the number of beats recorded in the ventricular fibrillation (VF) counter is greater than the value of the VF threshold, or if each of the morphology, long duration standard deviation, and short duration standard deviation thresholds are exceeded, then control passes to a block 700, wherein a signal indicating the detection of ventricular fibrillation is produced.

Control then passes to a decision block 705 to determine if ventricular tachycardia has already been detected. If so, control passes to a process block 710, wherein the ventricular tachycardia detection variables are set so that ventricular tachycardia is no longer indicated as detected. This is done so that the detection of ventricular fibrillation will supersede the detection of ventricular tachycardia. This is important since the treatments for ventricular fibrillation and ventricular tachycardia differ significantly, and electrical therapy should be administered for the more immediately life-threatening arrhythmia (ventricular fibrillation). It should be noted that ventricular flutter is detectable by the above described method, and these arrhythmias and asystole are grouped in the same category, so that the treatments for these arrhythmias are similar to that administered for ventricular fibrillation. Control then passes from the process block 710 to the process block 720. If ventricular fibrillation is not detected in the decision block 705, then control passes directly to the process block 720 without modifying the ventricular tachycardia detection variables.

Within the process block 720, general housekeeping chores which accompany such methods as that detailed above are performed. For example, selected variables may be incremented, while others may be reset. In addition, control passes to a separate tasking procedure, described above with reference to FIGS. 3A-3C, which initiates and controls the administration of the therapeutic electrical pulses.

As explained above, the parameters and detection thresholds for the various arrhythmias, as well as the levels of therapeutic energy supplied via the delivery electrodes 133 and 134, may be programmed by the attending physician to values and levels which are determined appropriate for the specific characteristics and condition of the individual patient. Therefore, the intervals, threshold values, monitoring duration periods, and step therapy energy levels administered in response to detected arrhythmias are merely exemplary and are not intended to limit the present invention.

Although the administration of electrical therapy has been described as being automatic, the present system also provides the capability of manually administering therapy in accordance with the detected arrhythmia. As seen in FIG. 2, the control and display panel 124 has a mode control 213, discharge controls 218, a charge control 215, an energy select control 214 and a ready-to-discharge indicator 206 which facilitate manual administration of electrical therapy. In such a case, the mode control 213 would be set to manual, and the energy level would be selected via the energy select control 214. The operator would initiate charging of the capacitor by depressing the charge control 215. Once an indication is provided via the ready-to-discharge indicator 206, the operator can discharge the capacitor, and thereby provide electrical therapy by depressing simultaneously the discharge controls 218. Alternatively, as is well known in the art, the system could be adapted to utilize conventional electrical therapy paddles which could be applied to the patient, and discharge could be implemented by discharge controls on the paddles.

Finally, as introduced above, the system 100 may include the infusion pump 141 configured to administer drug therapy to the patient 110. The system 100 may be provided with the cardioverter/defibrillator circuitry 130 in one embodiment, with the infusion pump 141 in another embodiment, and with both the cardioverter/defibrillator circuitry 130 and the infusion pump in yet another embodiment. The infusion pump could therefore be used instead of or in combination with the cardioverter/defibrillator 130 to deliver therapy to the patient 110.

The delivery of drug therapy is somewhat similar to the electrical therapy. For instance, the system 100 may detect ventricular tachycardia, and instead of delivering electrical therapy, the microprocessor 120 would activate the infusion pump to deliver a therapeutic drug. The dosage administered may depend on the drug chosen by the physician and the arrhythmia detected. Parameters regarding the dosage in relationship to the patient and the condition are programmable by the attending physician in order to configure the proper therapy.

The drug therapy could also be delivered in combination with the electrical therapy. As is well known in the art, under certain circumstances, drug administration is often utilized in combination with electrical therapy in order to convert a patient suffering from an abnormal heart rhythm to normal sinus rhythm. In an embodiment which provides both capabilities, the specifics of the electrical therapy and drug therapy are controlled via the programmable parameters.

Thus, the present invention provides an integrated method and apparatus for monitoring, detecting, and treating conditions of ventricular fibrillation, ventricular tachycardia, and other associated conditions precipitated by the onset of electrical instabilities of the heart muscle. It should be noted that the apparatus and method of the present invention may be implemented in a variety of ways. For example, a number of different sensors, other than those specifically mentioned here, may be employed to ascertain the cardiac condition of the patient. Similarly, other circuit elements which perform the same or similar functions as those described herein may be used to implement the present invention. In addition, the particular method outlined above for detecting the QRS complex, determining the presence of an arrhythmia, and determining the type of arrhythmia may be modified while still retaining the general sense of the invention. Therefore, the foregoing description should be construed as merely illustrative and in no way restrictive to the spirit and scope of the present invention. Furthermore, other embodiments and modifications of the invention may be conceived which fall within the scope and range of equivalency of the appended claims. Accordingly, the scope of the invention, including all embodiments and their equivalents, should be understood in light of the appended claims.

What is claimed is:

1. A programmable external cardioverter/defibrillator device for automatically detecting cardiac arrhythmias and administering therapy, said device effectively discriminating between signals received from a patient that represent the actual condition of a patient's heart and signal noise or artifact, said system being further adaptable in detection and therapy from patient to patient, said system comprising:

at least one external sensor, said sensor detecting cardiac signals from outside of the body of the patient and producing a detection signal representing said cardiac signals;

a signal noise and artifact discrimination controller connected to receive said detection signal, wherein said controller filters noise and artifact from the detection signal and generates a filtered detection signal so that the system can accurately detect the actual condition of the patient's heart;

programmable control circuitry having an alterable parameter memory adapted to receive and store vital parameters which are changeable by an operator, said control circuitry further having processing logic coupled to said parameter memory and to said signal noise and artifact discrimination controller, wherein said processing logic receives said filtered detection signal and is responsive to said filtered detection signal and the parameters in said parameter memory to automatically detect and identify types of cardiac arrhythmias, said processing logic further automatically selecting a first predetermined energy to be delivered for electrical therapy when a life-threatening arrhythmia is detected, wherein said first predetermined energy is selected based upon the type of arrhythmia identified, said processing logic further monitoring the filtered detection signal for a time interval sufficient to determine if cardioversion or defibrillation has occurred after said first predetermined energy has been delivered to said patient, and automatically selecting and delivering a second predetermined energy having a level at least equal to a level of said first predetermined energy if cardioversion or defibrillation has not occurred, wherein said processing logic generates control signals indicating the energy level when an arrhythmia has been detected; and cardioverter/defibrillator circuitry coupled to said processing logic and to said at least two energy delivery electrodes, wherein said cardioverter/defibrillator circuitry is responsive to said control signals received from said processing logic to automatically deliver therapeutic electrical stimuli via said energy delivery electrodes at the first predetermined energy when an arrhythmia has been detected, and at said second predetermined energy when an arrhythmia persists after delivery of said first predetermined energy.

2. A programmable external cardioverter/defibrillator device for automatically detecting cardiac arrhythmias and administering therapy, said device effectively discriminating between signals received from a patient that represent the actual condition of a patient's heart and signal noise or artifact, said system being further adaptable in detection and therapy from patient to patient, said system comprising:

at least one external sensor which detects cardiac signals from outside of the body of the patient and produces a detection signal representing said cardiac signals;

signal noise and artifact discrimination circuitry and control connected to said at least one external sensor to filter noise and artifact from the detection signal, wherein said signal noise and artifact discrimination circuitry and control generates a filtered detection signal so that the system can accurately detect the actual condition of the patient's heart;

programmable control circuitry having an alterable parameter memory adapted to receive and store vital parameters which are changeable by an operator, said control circuitry further having processing logic coupled to said parameter memory and to said signal noise and artifact discrimination circuitry and control, wherein said processing logic receives said filtered detection signal and is responsive to said filtered detection signal and the parameters in said parameter memory to detect arrhythmias and to produce control signals indicating whether an arrhythmia has been detected;

cardioverter/defibrillator circuitry connected to said processing logic, wherein said cardioverter/defibrillator circuitry is responsive to said control signals to automatically generate therapeutic electrical stimuli at varying levels of intensity when a life threatening arrhythmia has been detected by said processing logic; and at least two energy delivery electrodes coupled to said cardioverter/defibrillator circuitry to deliver the therapeutic electrical stimuli at varying levels.

3. The external cardioverter/defibrillator device of claim 2, further comprising external programming means for programming and modifying said vital parameters, said external programming means coupled to said programmable control circuitry.

4. The external cardioverter/defibrillator device of claim 2, wherein the processing logic includes at least one counter for monitoring a number of heart beats which occur during a predetermined time interval, wherein said processing logic identifies the type of arrhythmia when an arrhythmia is detected based upon the number of beats counted.

5. The external cardioverter/defibrillator device of claim 2, further comprising a drug infusion pump coupled to said patient and to said programmable control circuitry, wherein said drug infusion pump is responsive to said control signals to administer therapeutic drugs to said patient.

6. A programmable external abnormal heart rhythm treatment device for automatically detecting cardiac arrhythmias and administering corrective therapy, said device being adaptable in the detection of arrhythmias and the administered treatment, said device comprising:

at least one external sensor for detecting cardiac signals outside of the body of the patient and producing a detection signal representing said cardiac signals;

signal noise and artifact discrimination circuitry and control connected to said at least one external sensor to filter noise and artifact from the detection signal., wherein said signal noise and artifact discrimination circuitry and control generates a filtered detection signal so that the system can accurately detect the actual condition of the patient's heart;

programmable control circuitry having an alterable parameter memory adapted to receive and store vital parameters which are changeable by an operator, said control circuitry further having processing logic coupled to said parameter memory and to said at least one sensor, wherein said processing logic receives said detection signal and is responsive to said detection signal and the parameters in said parameter memory to produce control signals indicating whether an arrhythmia has been detected; and a drug therapy infusion pump coupled to said programmable control circuitry and responsive to said control signals to infuse therapeutic drugs to said patient when an arrhythmia has been detected.

7. The programmable external abnormal heart rhythm treatment device of claim 6, wherein the control signals received from the control circuitry further indicate the dosage of said therapeutic drugs to be delivered to said patient.

8. A method for effecting therapeutic cardioversion or defibrillation of a cardiac arrhythmia using a programmable external cardioverter/defibrillator as defined in claim 4, said method comprising the steps of:

applying said at least one external sensor to the body of said patient;

externally applying said at least two energy delivery electrodes to said patient;

monitoring said filtered detection signal generated by said signal noise and artifact discrimination circuitry to automatically detect and identify the cardiac arrhythmia;

automatically selecting a first predetermined energy to be delivered for electrical therapy based upon the type of the arrhythmia detected;

producing a control signal indicating that an arrhythmia has been detected, wherein said cardioverter/defibrillator circuitry is responsive to said control signal to automatically apply an electrical stimulus through the energy delivery electrodes to deliver said first predetermined energy to said patient via said at least two energy delivery electrodes;

monitoring the filtered detection signal for a time interval sufficient to determine if cardioversion or defibrillation has occurred after delivery of said electrical stimulus; and if said first predetermined energy level is not less than a maximum predetermined energy level, and if cardioversion or defibrillation has not occurred, selecting a subsequent predetermined energy level at least equal to said first predetermined energy level and repeating said applying and monitoring steps with said subsequent predetermined energy level.

9. The method of claim 8, further comprising the steps of:

determining the impedance between the at least two energy delivery electrodes; and adjusting a selected voltage level to be applied as the electrical stimulus across said energy delivery electrodes in response to said determined impedance so that the voltage applied delivers the first predetermined energy level and the subsequent predetermined energy level.

10. The method of claim 8, further comprising the steps of:

if cardioversion or defibrillation has not occurred, with said cardioverter/defibrillator, repeatedly and automatically selecting an additional predetermined energy having a level at least equal to said first predetermined energy level and repeating said applying and monitoring steps with said additional predetermined energy level until cardioversion or defibrillation has occurred or until the additional predetermined energy equals the maximum predetermined energy; and when said additional predetermined energy equals the maximum predetermined energy, repeating said applying and monitoring steps with the maximum predetermined energy until cardioversion or defibrillation has occurred or until a maximum number of therapies have been delivered.

11. A method for treating cardiac arrhythmias using the programmable external abnormal heart rhythm treatment device defined in claim 6, said method comprising the steps of:

applying said at least one external sensor to the body of said patient;

connecting said infusion pump to said patient;

monitoring said detection signal to automatically detect and identify the cardiac arrhythmia;

producing a control signal indicating that an arrhythmia has been detected, wherein said infusion pump is responsive to said control signal to to deliver a first dosage of drug therapy to a patient based upon the type of arrhythmia detected;

monitoring the detection signal for a time interval sufficient to determine if a return to a non-treatable rhythm has occurred after delivery of said drug therapy; and if said first dosage is not less than a maximum dosage level, and if return to a non-treatable rhythm has not occurred, selecting a subsequent dosage level greater than said first dosage level and repeating said activating and monitoring steps with said subsequent dosage level.

12. A method for effecting therapeutic cardioversion or defibrillation of a cardiac arrhythmia using an external cardioverter/defibrillator device, said method comprising the steps of:

applying said at least one external sensor to the body of said patient;

externally applying said energy delivery electrodes to the body of said patient;

monitoring said detection signal produced by said at least one sensor to automatically detect and identify the cardiac arrhythmia;

automatically selecting a first predetermined energy to be delivered for electrical therapy based upon the type of the arrhythmia detected;

generating a control signal indicating that an arrhythmia has been detected, wherein said cardioverter/defibrillator circuitry is responsive to said control signal to automatically apply an electrical stimulus through the energy delivery electrodes to deliver said first predetermined energy to said patient via said at least two energy delivery electrodes.

13. The method of claim 12, further comprising the steps of:

monitoring the detection signal for a time interval sufficient to determine if cardioversion or defibrillation has occurred after delivery of said electrical stimulus; and if said first predetermined energy level is less than a maximum predetermined energy level, and if cardioversion or defibrillation has not occurred, selecting a subsequent predetermined energy level at least equal to said first predetermined energy level and repeating said applying and monitoring steps with said subsequent predetermined energy level.

14. An external cardioverter/defibrillator device for automatically detecting cardiac arrhythmias and administering therapy to a patient, said device effectively discriminating between signals received from a patient that represent the actual condition of a patient's heart and signal noise or artifact, said system comprising:

at least one external sensor for detecting cardiac signals from outside of the body of the patient and producing a detection signal representing said cardiac signals;

programmable control circuitry having an alterable parameter memory adapted to receive and store vital parameters which are changeable by an operator, said control circuitry further having processing logic coupled to said parameter memory and to said at least one external sensor, wherein said processing logic is responsive to said detection signal and the parameters in said parameter memory to automatically detect and identify types of cardiac arrhythmias, said processing logic further automatically selecting a first predetermined energy to be delivered for electrical therapy when a life-threatening arrhythmia is detected, wherein said first predetermined energy is selected based upon the type of arrhythmia identified, said processing logic further monitoring the detection signal for a time interval sufficient to determine if cardioversion or defibrillation has occurred after said first predetermined energy has been delivered to said patient and automatically selecting and delivering a second predetermined energy having a level at least equal to a level of said first predetermined energy if cardioversion or defibrillation has not occurred, wherein said processing logic generates control signals indicating the energy level when an arrhythmia has been detected; and cardioverter/defibrillator circuitry coupled to said processing logic and at least two energy delivery electrodes, wherein said cardioverter/defibrillator circuitry is responsive to said control signals received from said processing logic to automatically deliver therapeutic electrical stimuli via said energy delivery electrodes at the first predetermined energy when an arrhythmia has been detected and at said second predetermined energy when an arrhythmia persists after delivery of said first predetermined energy.

* * * * *

UNITED STATES PATENT AND TRADEMARK OFFICE
CERTIFICATE OF CORRECTION

PATENT NO. : 5,474,574
DATED : December 12, 1995
INVENTOR(S) : Errol G. Payne, et al.

It is certified that error appears in the above-indentified patent and that said Letters Patent is hereby corrected as shown below:

Column 17, Line 34 -  delete "2x" insert — 2X —

Column 22, Line 51 -  delete the "." after the word "signal"

Signed and Sealed this

Tenth Day of September, 1996

Attest:

BRUCE LEHMAN

Attesting Officer  Commissioner of Patents and Trademarks